(12) United States Patent
Lacey

(10) Patent No.: US 7,662,912 B2
(45) Date of Patent: Feb. 16, 2010

(54) POLYOMAVIRUS DIAGNOSTIC REAGENTS

(75) Inventor: Simon F. Lacey, Glendora, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 12/273,808

(22) Filed: Nov. 19, 2008

(65) Prior Publication Data
US 2009/0099335 A1    Apr. 16, 2009

Related U.S. Application Data

(62) Division of application No. 11/491,542, filed on Jul. 24, 2006, now Pat. No. 7,468,186.

(60) Provisional application No. 60/701,484, filed on Jul. 22, 2005.

(51) Int. Cl.
*C08J 3/28* (2006.01)

(52) U.S. Cl. .................................................. 530/300

(58) Field of Classification Search ........................ None
See application file for complete search history.

(56) References Cited

U.S. PATENT DOCUMENTS

| 5,734,023 | A | 3/1998 | Nag et al. | |
|---|---|---|---|---|
| 7,517,520 | B2 * | 4/2009 | Manolova et al. | 424/93.2 |
| 2003/0044961 | A1 | 3/2003 | Luke et al. | |

OTHER PUBLICATIONS

Anonymous. Microbiology@Leicester: Virology: Polyomaviruses: (www-micro.msb.le.ac.uk/3035/Polyomaviruses.html; 2004 (14 pgs.).
Siegel, "Polyomaviridae 2004" (www.stanford.edu/group/virus/polyoma/2004temple/polyoma.html (6 pgs.).
Comoli, Patrizia et al., "Dendritic cells pulsed with polyomavirus BK antigen induce Ex Vivo polyoma BK virus-specific cytotoxic t-cell lines in seropositive healthy individuals and renal transplant recipients," Journal of the American Society of Nephrology, 14: 3197-3204, 2003.
Comoli, Patrizia et al., "Polyomavirus BK-specific immunity after kidney transplantation," Transplantation, 78(8): 1229-1232, 2004.
Du Pasquier, R. A. et al., "A prospective study demonstrates an association between JC virus-specific cytotoxic T lymphocytes and the early control of progressive multifocal leukoencephalopathy," Brain, 127(9): 1970-1978, 2004.
Du Pasquier, R. A. et al., "Detection of JC virus-specific cytotoxic T lymphocytes in healthy individuals," Journal of Virology, 78(18): 10206-10210, 2004.
Du Pasquier, R. A. et al., "JCV-specific cellular immune response correlates with a favorable clinical outcome in HIV-infected individuals with progressive multifocal leukoencephalopathy," Journal of NeuroVirology, 7: 318-322, 2001.
Du Pasquier, R. A. et al., "Low frequency of cytotoxic T lymphocytes against the novel HLA-A*0201-restricted JC virus epitope VP1(p36) in patients with proven or possible progressive multifocal Leukoencephalopathy," Journal of Virology, 77(22): 11918-11926, 2003.
Garcea, Robert L. et al., "Minireview: Simian virus 40 infection of humans," Journal of Virology, 77(9): 5039-5045, 2003.
Hirsch, Hans H. et al., "Polyomavirus BK," The Lancet, 3: 611-623, 2003.
Koralnik, Igor J. et al., "JC virus-specific cytotoxic T lymphocytes in individuals with progressive multifocal leukoencephalopathy," Journal of Virology, 75(7): 3483-3487, 2001.
Koralnik, Igor J. et al., "Association of prolonged survival in HLA-A2+ progressive multifocal leukoencephalopathy patients with a CTL response specific for a commonly recognized JC virus epitope," The Journal of Immunology, 168(1): 499-504, 2002.
Lacey, Simon F. et al., "Characterization of cytotoxic function of CMV-pp65-Specific CD8+ T-Lymphocytes identified by HLA tetramers in recipients and donors of stem-cell transplants," Transplantation, 74(5): 722-732, 2002.
McDowall, J., "SV40" (www.ebi.ac.uk/interpro/potm/2003 6/Page1.htm; 2003 (3 pgs.).
Viscidi, R. P. et al., "Serological cross-reactivities between antibodies to simian virus 40, BK virus, and JC virus assessed by virus-like-particle-based enzyme immunoassays," Clinical Diagnostic Laboratory Immunology, 10(2): 278-285, 2003.
Bakker et al. "MHC Multimer Technology: Current Status and Future Prospects" Current Opinion in Immunology 17:428-433, 2005.
Bieganowska et al. "Direct Analysis of Viral-Specific CD8+ T Cells with Soluble HLA-A2/Tax11-19 Tetramer Complexes in Patients with Human T Cell Lymphotropic Virus-Associated Myelopathy[1]" The Journal of Immunology 162:1765-1771, 1999.
Holman et al. "Characterizing the Impact of CD8 Antibodies on Class I MHC Multimer Binding[1]" Journal of Immunology 174:3986-3991, 2005.
Knabel et al. "Reversible MHC Multimer Staining for Functional Isolation of T-Cell Populations and Effective Adoptive Transfer" Nature Medicine 8:(6):631-637, 2002.
Krausa et al. "A Comprehensive PCR-SSP Typing System for Identification of HLA-A Locus Alleles" Tissue Antigens 47:237-244, 1996.
Lacey et al. "Characterization of Cytotoxic Function of CMV-pp65-Specific CD8+ T-Lymphocytes Identified by HLA Tetramers in Recipients and Donors of Stem-Cell Transplants" Transplantation 74:(5) 722-732, 2002.
Lebowitz et al. "Soluble, High-Affinity Dimers of T-Cell Receptors and Class II Major Histocompatibility Complexes: Biochemical Probes for Analysis and Modulation of Immune Responses" Cellular Immunology 192:175-184, 1999.
Sun et al. "MHC Class I Multimers" Arthritis Res. 3:265-269, 2001.

* cited by examiner

*Primary Examiner*—Ali R. Salimi
(74) *Attorney, Agent, or Firm*—Rothwell, Figg, Ernst & Manbeck, P.C.

(57) ABSTRACT

The present invention relates to HLA-A*02-restricted cellular epitopes within the VP1 polypeptide of human polyomaviruses, which are useful as diagnostic reagents for virus infection. Preferred peptides correspond to amino acids residues 107-116, 108-116 and 44-52 of BKV VP1, and are processed in vivo in natural infection with BKV. Effector T cell populations stimulated by the peptides represent functional CTLs as assessed by cytotoxicity and cytokine production, and are reactive against cells presenting both the BKV peptides above and the JC virus homolog sequences.

10 Claims, 20 Drawing Sheets

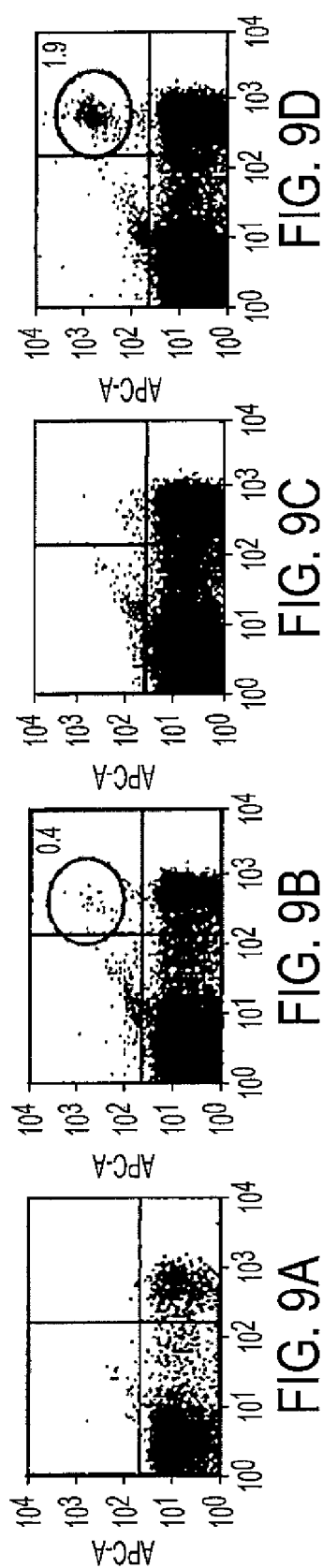

DEGRANULATION (α-CD107a/b-FITC)

α-IFN-γ-PE

αCD8-FITC

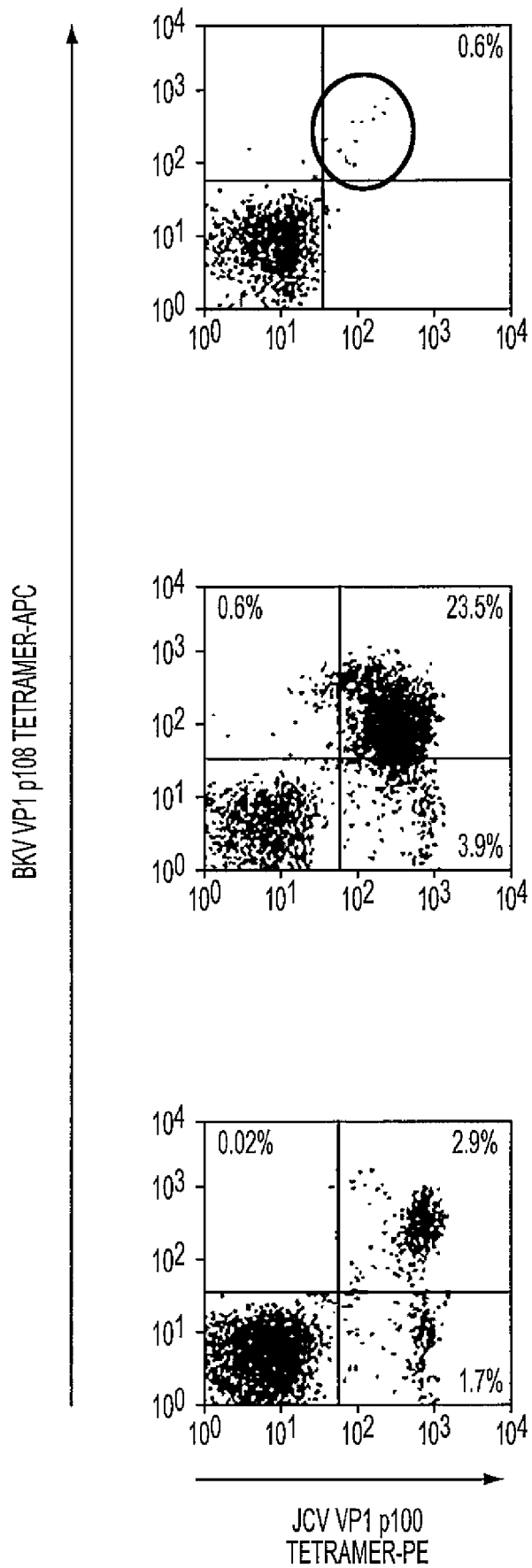

SEQUENCE LISTING

```
<160> NUMBER OF SEQ ID NOS: 14

<210> SEQ ID NO 1
<211> LENGTH: 9
<212> TYPE: PRT
<213> ORGANISM: Polyomavirus hominis 1

<400> SEQUENCE: 1

Leu Leu Met Trp Glu Ala Val Thr Val
1               5

<210> SEQ ID NO 2
<211> LENGTH: 10
<212> TYPE: PRT
<213> ORGANISM: Polyomavirus hominis 1
```

-continued

```
<400> SEQUENCE: 2

Asn Leu Leu Met Trp Glu Ala Val Thr Val
1               5                   10

<210> SEQ ID NO 3
<211> LENGTH: 9
<212> TYPE: PRT
<213> ORGANISM: Polyomavirus hominis 2

<400> SEQUENCE: 3

Ile Leu Met Trp Glu Ala Val Thr Leu
1               5

<210> SEQ ID NO 4
<211> LENGTH: 9
<212> TYPE: PRT
<213> ORGANISM: Simian virus 40

<400> SEQUENCE: 4

Ile Leu Met Trp Glu Ala Val Thr Val
1               5

<210> SEQ ID NO 5
<211> LENGTH: 9
<212> TYPE: PRT
<213> ORGANISM: Polyomavirus hominis 1

<400> SEQUENCE: 5

Ala Ile Thr Glu Val Glu Cys Phe Leu
1               5

<210> SEQ ID NO 6
<211> LENGTH: 9
<212> TYPE: PRT
<213> ORGANISM: Polyomavirus hominis 2

<400> SEQUENCE: 6

Ser Ile Thr Glu Val Glu Cys Phe Leu
1               5

<210> SEQ ID NO 7
<211> LENGTH: 9
<212> TYPE: PRT
<213> ORGANISM: Simian virus 40

<400> SEQUENCE: 7

Ser Phe Thr Glu Val Glu Cys Phe Leu
1               5

<210> SEQ ID NO 8
<211> LENGTH: 10
<212> TYPE: PRT
<213> ORGANISM: Polyomavirus hominis 1

<400> SEQUENCE: 8

Lys Leu Leu Ile Lys Gly Gly Val Glu Val
1               5                   10

<210> SEQ ID NO 9
<211> LENGTH: 9
<212> TYPE: PRT
<213> ORGANISM: Polyomavirus hominis 1
```

```
-continued

<400> SEQUENCE: 9

Leu Leu Ile Lys Gly Gly Val Glu Val
1               5

<210> SEQ ID NO 10
<211> LENGTH: 10
<212> TYPE: PRT
<213> ORGANISM: Polyomavirus hominis 1

<400> SEQUENCE: 10

Leu Leu Ile Lys Gly Gly Val Glu Val Leu
1               5                   10

<210> SEQ ID NO 11
<211> LENGTH: 10
<212> TYPE: PRT
<213> ORGANISM: Polyomavirus hominis 1

<400> SEQUENCE: 11

Leu Met Trp Glu Ala Val Thr Val Gln Thr
1               5                   10

<210> SEQ ID NO 12
<211> LENGTH: 9
<212> TYPE: PRT
<213> ORGANISM: Human immunodeficiency virus

<400> SEQUENCE: 12

Ile Leu Lys Glu Pro Val Asn Gly Val
1               5

<210> SEQ ID NO 13
<211> LENGTH: 9
<212> TYPE: PRT
<213> ORGANISM: Human cytomegalovirus

<400> SEQUENCE: 13

Gln Ile Lys Val Arg Val Asp Met Val
1               5

<210> SEQ ID NO 14
<211> LENGTH: 9
<212> TYPE: PRT
<213> ORGANISM: Human cytomegalovirus

<400> SEQUENCE: 14

Asn Leu Val Pro Met Val Ala Thr Val
1               5
```

POLYOMAVIRUS DIAGNOSTIC REAGENTS

This application is a divisional of prior co-pending U.S. application Ser. No. 11/491,542, filed Jul. 24, 2006, which claims the benefit of prior co-pending U.S. Provisional Application Ser. No. 60/701,484, filed Jul. 22, 2005. Both of these applications are hereby incorporated by reference in its entirety.

STATEMENT REGARDING FEDERALLY SPONSORED RESEARCH

This invention was made with government support in the form of grants no. 1R21CA104261-01 from the National Cancer Institute of the United States Department of Health and Human Services, National Institutes of Health. The United States government may have certain rights in the invention.

BACKGROUND OF THE INVENTION

1. Technical Field

This invention relates to the field of medical sciences, in particular the field of immunology and viral immunity. Specifically, the invention relates to cellular epitopes of the VP1 polypeptide of polyomaviruses, for example BK virus, JC virus and SV40.

2. Description of the Background Art

Polyomavirus hominis 1, known as BK virus (BKV), is a ubiquitous human polyomavirus that causes asymptomatic primary infection and resides, latent, in several body sites, notably the kidney and genitourinary tract. See Stolt et al., *J. Gen. Virol.* 84:1499-1504, 2003. BKV, the related polyomavirus hominis 2 (also known as JC virus or JCV) and simian vacuolating virus 40 (SV40) are closely related species of the genus polyomavirus. The BKV genome is about 75% homologous overall to JCV and about 70% homologous overall to SV40.

Primary BKV infection during childhood is presumed to occur via the respiratory tract. Following infection, hematologous dissemination is postulated to occur. Persistence is preferentially within the genitourinary tract (renal epithelial cells and the lower genitourinary tract (bladder, ureters)). Chesters et al., *J. Infect. Dis.* 147:676-684, 1983. BKV reactivation often occurs in immunocompromised individuals such as hematopoietic stem cell transplant and kidney transplant recipients, causing clinical disease states which include hemorrhagic cystitis, ureteric stenosis and polyomavirus-associated nephropathy (PVAN, also referred to as BK virus-associated nephropathy (BKVN)). The incidence of polyomavirus-associated nephropathy, variously reported as between 1% and 8% of kidney transplant patients, has increased in recent years, concomitant with the use of newer and more potent immunosuppressive agents in transplant patients, suggesting that immune responses to BKV are important in control of the virus. Hirsch and Steiger, *Lancet* 3:611-623, 2003.

Polyomavirus associated nephropathy now is recognized as an important cause of allograft dysfunction in kidney transplant recipients. Binet et al., *Transplantation* 678:918-922, 1999; Hurault et al., *Transplant Proc.* 32:2760-2761, 2000; Randawa et al., *Transplantation* 67:103-109, 1999. With immunosuppression, viral reactivation can occur, presumably primarily from the lower genitourinary tract, and is detected as virus shed in the urine (viruria). With continued immunosuppression and other local injury within the kidney, such as rejection or calcineurin inhibitor toxicity, polyomavirus reactivation also can occur in the kidney itself, leading to viral replication, direct injury to the infected tubular epithelial cells and indirect injury manifested by inflammation and nephritis, ultimately leading to rejection of the kidney in some cases. In kidney transplant recipients, BKV reactivation is particularly associated with interstitial nephritis/nephropathy and ureteric stenosis. Nickeleit et al., *J. Am. Soc. Nephrol.* 10:1080-1089, 1999; Nickeleit et al., *Nephrol. Dial. Transplant.* 15:324-332, 2000.

Other than the antiviral agent, cidofovir, for treatment of PVAN, no other antiviral therapies are available for polyomavirus. Kadambi et al., *Am. J. Transplant.* 3:186-191, 2003; Scantlebury et al., *Graft* 5(supp):S82-S87, 2002; Vats et al., *Transplantation* 75:105-112, 2003. Cidofovir requires intravenous administration and is associated with considerable nephrotoxicity itself, particularly in patients with pre-existing nephrotoxicity. Based on a consensus opinion that PVAN may represent a state of relative over-immunosuppression, the current approach to managing patients with PVAN is reduction of immunosuppression. Even using this approach, however, up to 30-50% of patients with PVAN develop progressive polyomavirus infection and deterioration of kidney function, ultimately resulting in loss of the kidney allograft. Hirsch and Steiger, *Lancet* 3:611-623, 2004; Nickeleit et al., *Nephrol. Dial. Transplant.* 15:324-332, 2000; Randhawa et al., *Transplantation* 67:103-109, 1999. Given the limited treatment options, there is an urgent need for alternative approaches to protect against BKV reactivation and disease.

JCV also is prevalent worldwide, with about 80% of adults showing serological evidence of JCV infection. Stolt et al., *J. Gen. Virol.* 84:1499-1504, 2003. Most individuals are infected in childhood, without showing any symptoms. The virus remains latent in the lymphocytes, urogenital tract and brain and can reactivate in the immunocompromised, causing disease syndromes. JCV is the causative agent of progressive multifocal leukoencephalopathy (PML), a fatal degenerative disease affecting brain oligodendroglial cells seen in immunosuppressed AIDS, cancer and organ transplant recipient patients. JCV also is associated with hemorrhagic cystitis and nephritis in kidney transplant recipients.

SV40 is a closely related polyomavirus of simians which also widely infects humans and has been associated with some tumor types. This virus has a high degree of serological cross-reactivity with both BKV and JCV antigens. SV40 is believed to spread through a respiratory or fomite route and to be established as a human pathological agent. Its presumed site of persistence also is the kidney, and other tissues that give rise to SV40-associated tumors (e.g., mesothelioma, lymphoma, osteosarcoma, and certain brain tumors).

The capsid of polyomavirus is largely made up of VP1, VP2 and VP3, with each virion containing 360 copies of VP1. Two cellular epitopes of JCV VP1 have been identified, including the epitope sequences, ILMWEAVTL (JCV $VP1_{p100-108}$; SEQ ID NO:3; referred to herein as "JC100") and SITEVECFL (JCV VP1p36-44; SEQ ID NO:6; referred to herein as "JC36"). Du Pasquier et al., *J. Neurovirol.* 7:318-322, 2001; Du Pasquier et al., *J. Virol.* 77:11918-11926, 2003; Du Pasquier et al., *Brain* 127(9):1970-1978, 2004; Du Pasquier et al., *J. Virol.* 78:10206-10, 2004; Koralnik et al., *J. Immunol.* 168:499-504, 2002; Koralnik et al., *J. Virol.* 75:3483-3487, 2001. CTL recognizing these epitopes have been associated with control of the virus; patients suffering from the JCV syndrome, progressive multifocal leukoencephalopathy, demonstrate a prolonged survival when they possess CTL responses to the JC100 epitope. Du Pasquier et al., *Brain* 127(9):1970-1978, 2004; Koralnik et al., *J. Immunol.* 168:499-504, 2002. BKV-specific cells also have been detected in samples from renal transplant patients. Comoli et al., *Transplantation* 78:1229-1232, 2004. These prior studies, which used BKV-infected cell lysates as antigens, did not identify any specific antigens or epitopes, however. BKV-specific T-cell lines have been developed from healthy seropositive individuals and kidney transplant recipients. Comoli et al., *Transplantation* 78:1229-1232, 2004; Comoli et al., *J. Am. Soc. Nephrol.* 14:3197-3204, 2003; Drummond et al., *J. Med. Virol.* 17:237-247, 1985; Drummond et al., *J. Med. Virol.* 23:331-344, 1987.

Several previous studies have shown that both JCV and BKV are common in most adult populations, but that JCV is less prevalent than BKV. Knowles et al., *J. Med. Virol.* 71:115-123, 2003; Padgett et al., *J. Infect. Dis.* 127:467-470, 1973; Taguchi et al., *Microbiol. Immunol.* 26:1057-1064, 1982. Knowles and colleagues reported 81% seropositivity for BKV and 35% for JCV in a survey of 2,435 sera from 1991. Knowles et al., *J. Med. Virol.* 71:115-123, 2003. These types of studies are complicated by substantial serological crossreactivities between antibodies to these two human polyomaviruses. Viscidi et al., *Clin. Diagn. Lab Immunol.* 10:278-285, 2003. However, antibody adsorption studies show that some individuals experience infection by both JCV and BKV. This is further supported by PCR studies of polyomavirus shedding in urine that indicate co-infection in a minority of patients. Bendiksen et al., *J. Gen. Virol.* 81:2625-2633, 2000; Hamilton et al., *J. Clin. Microbiol.* 38:105-109, 2000; Priftakis et al., *J. Clin. Microbiol.* 38:406-407, 2000; Shah et al., *J. Infect. Dis.* 176:1618-1621, 1997.

Knowledge of specific MHC—I restricted epitopes within BK virus antigens allows one to track virus-specific CTLs in at-risk patients and produce compositions to modify immunity to BK and related viruses such as JCV and SV40. Peptides identified as immunoreactive are useful for vaccines as well as diagnostic reagents. Vaccine peptides from viral proteins may be used for enhancing the immune system of mammals with respect to the virus in both seropositive and seronegative individuals. However, no such specific information concerning BKV epitopes has been available. There is a need in the art for compositions and methods which can be used to identify and diagnose polyomavirus-related conditions in patients and patient-derived samples, and to modify the immune response of patients in need, such as immunosuppressed patients, or any person at risk for polyomavirus infection or reactivation.

SUMMARY OF THE INVENTION

Accordingly, the invention generally relates to a viral epitope useful for diagnosis and treatment of human polyomavirus. In one embodiment, the invention provides the isolated peptides LLMWEAVTV (SEQ ID NO:1), AITEVECFL (SEQ ID NO:5) and NLLMWEAVTV (SEQ ID NO:2). In other embodiments, the invention provides vaccine compositions against polyomavirus that comprise these peptides. Such vaccines are useful for polyomavirus prophylaxis and treatment, including BKV, JCV and SV40. Vaccines according to embodiments of the invention optionally also comprise an adjuvant, for example a DNA adjuvant and/or a T helper epitope such as PADRE. In addition, vaccines of the invention include antigen presenting cells that present the peptide LLMWEAVTV (SEQ ID NO:1), AITEVECFL (SEQ ID NO:5) or NLLMWEAVTV (SEQ ID NO:2) in one embodiment, or a viral vaccine that encodes LLMWEAVTV (SEQ ID NO:1), AITEVECFL (SEQ ID NO:5) or NLLMWEAVTV (SEQ ID NO:2).

In further embodiments, the invention provides a polyomavirus diagnostic reagent which comprises the peptide LLMWEAVTV (SEQ ID NO:1), AITEVECFL (SEQ ID NO:5) or NLLMWEAVTV (SEQ ID NO:2), for example a tetramer reagent.

In yet a further embodiment, the invention provides a method of expanding polyomavirus-specific cytotoxic T lymphocytes in a population of T lymphocytes which comprises contacting the population of T lymphocytes with antigen presenting cells that present the peptide LLMWEAVTV (SEQ ID NO:1), AITEVECFL (SEQ ID NO:5) or NLLMWEAVTV (SEQ ID NO:2) and such expanded polyomavirus-specific cytotoxic T lymphocytes.

In yet a further embodiment, the invention provides a method of modulating the immune response of a patient to a polyomavirus or immunotherapy for treatment of a polyomavirus-infected patient which comprises administering to the patient any of the vaccines discussed above and/or the polyomavirus-specific cytotoxic T lymphocytes discussed above.

BRIEF DESCRIPTION OF THE DRAWINGS

FIG. 1 provides results of a T2 stabilization/HLA-A02 binding assay comparing six BKV VP1 peptides and two control peptides. A: no peptide; B: BK26 (KLLIKGGVEV; SEQ ID NO:8); C: BK27a (LLIKGGVEVL; SEQ ID NO:10); D: BK27b (LLIKGGVEV; SEQ ID NO: 9); E: BK108 (LLMWEAVTV; SEQ ID NO:1); F: BK107 (NLLMWEAVTV; SEQ ID NO:2); G: BK109 (LMWEAVTVQT; SEQ ID NO:11); H: control peptide (ILKEPVNGV; corresponding to part of the HIV POL open reading frame; SEQ ID NO:12); I: control peptide (QIKVRVDMV; corresponding to a HLA-B*08-restricted epitope in the HCMV major immediate-early gene; SEQ ID NO:13).

FIG. 2 shows results of a cytotoxicity assay of the cells of FIG. 3 using JA2 cells loaded with BK108 or control HIV peptide. Diamond: BK108 peptide; square: control peptide.

FIG. 3 shows results of ICC assays on splenocytes from HHD-II mice immunized with BK108 peptide, the T helper peptide, PADRE, and CpG DNA adjuvant.

FIG. 4 shows results of a cytotoxicity assay of splenocytes from HHD-II mice immunized with rMVA expressing BKV VP1. These splenocytes were stimulated in vitro with BK108, and the cytotoxicity assays used JA2 cells loaded with BK108 or control HIV peptide as targets. Diamond: BK108 peptide; triangle: BK108 peptide: square: control peptide.

FIG. 5 shows ICC assay results of the cells described for FIG. 4.

FIG. 6 shows results of specific cytotoxicity of transgenic splenocytes expressing BKV VP1 using A2-Jurkat cells pulsed with the indicated peptides.

FIG. 7 shows results of an ICC assay of immunized transgenic mice splenocytes (rMVA-BKV VP1) stimulated in vitro with the peptides BK108 (7A), JC100 (7B) and control peptide (7C).

FIG. 8 shows the results of intracellular cytokine (ICC) assays for IFN-γ production on peptide stimulation of transgenic splenocytes expressing BKV VP1 with the indicated peptides.

FIG. 9 shows results of screening PBMC from healthy donors and kidney transplant recipients for CTL recognizing the BK108 epitope. All plots are gated on lymphocytes by forward vs. side scatter.

FIG. 10 shows the functionality of BK108 tetramer-binding cells from normal donor #07, labeled with CyChrome™-conjugated antibody to CD8.

FIG. 11 shows the functionality of BK108 tetramer-binding cells from normal donor #07, labeled with PE-conjugated antibody to IFN-γ.

FIG. 13 shows fluorescence-activated cell sorting results for PBMC and peptide-stimulated cell cultures from a kidney transplant recipient. The cells were labeled with both BK108tet-APC and JC100tet-PE.

Figure 14:
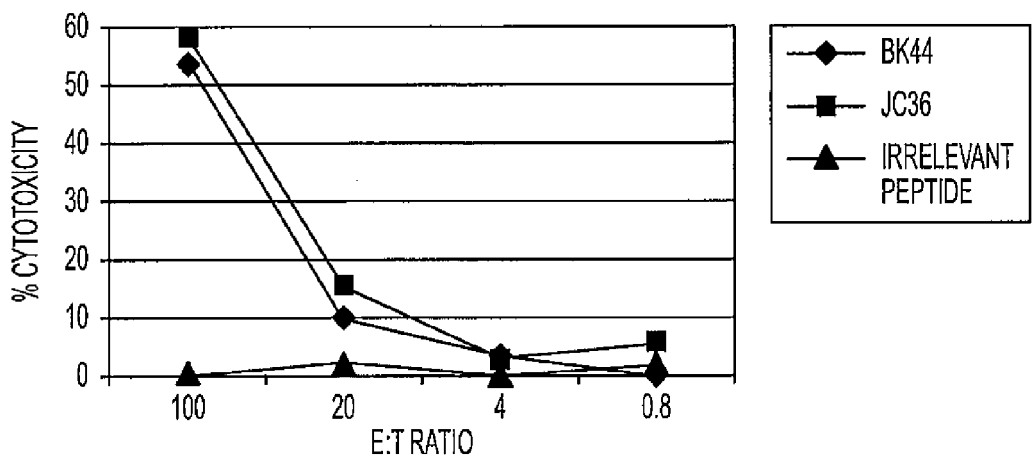
FIG. 14 shows representative results of a cytotoxicity assay for immune splenocytes against Jurkat A2 targets that had been pulsed with BK44 peptide, JC36 peptide or an irrelevant HIV peptide.
Figure 15A:
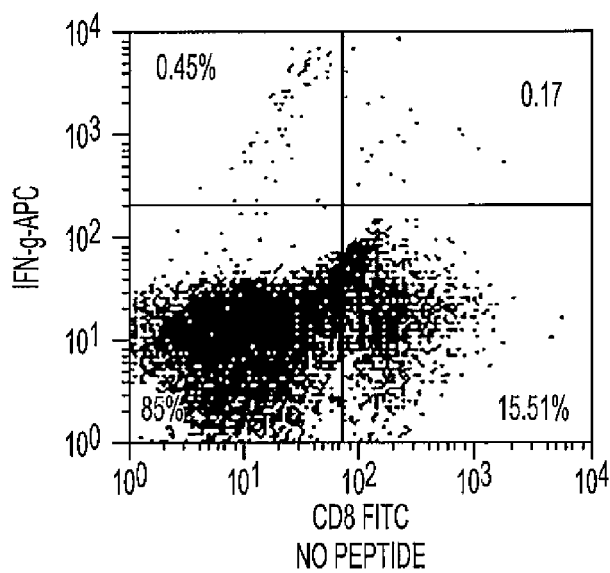
Figure 15B:
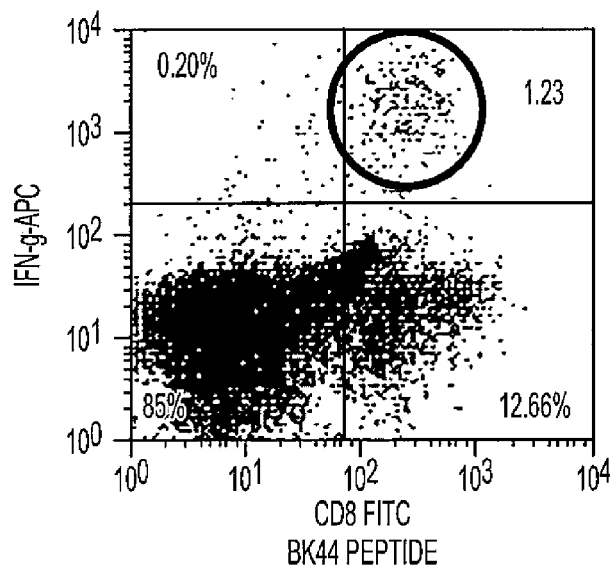

FIG. 15 provides results of an intracellular cytokine assay performed on the cells analyzed in FIG. 14.

Figure 16A:
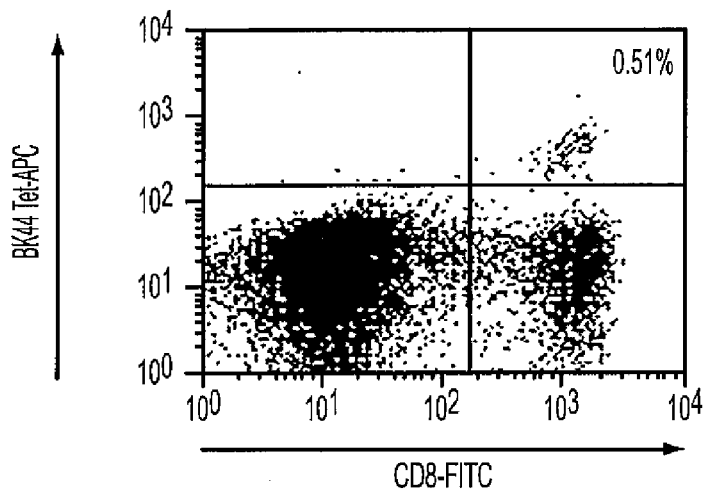
Figure 16B:
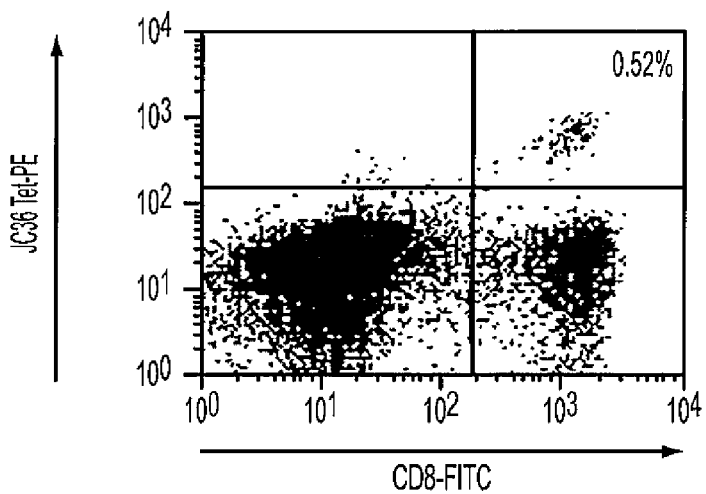

FIG. 16 provides data from flow analyses of an aliquot of PBMC from a normal donor, stimulated in culture with BK44 peptide in the presence of rIL2 and labeled with BK44tet-APC (FIG. 16A) or JC36tet-PE (FIG. 16B).

Figure 17:
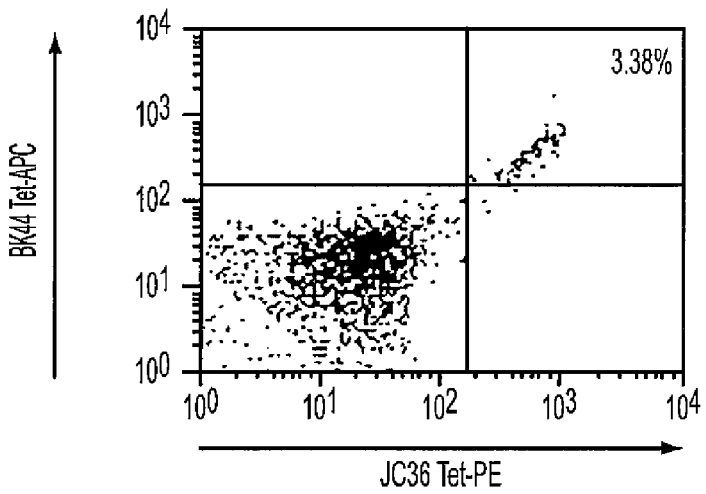

FIG. 17 provides data from flow analyses of an aliquot of PBMC from a normal donor, stimulated in culture with BK44 peptide in the presence of rIL2 and labeled with both BK44tet-APC and JC36tet-PE.

Figure 18:
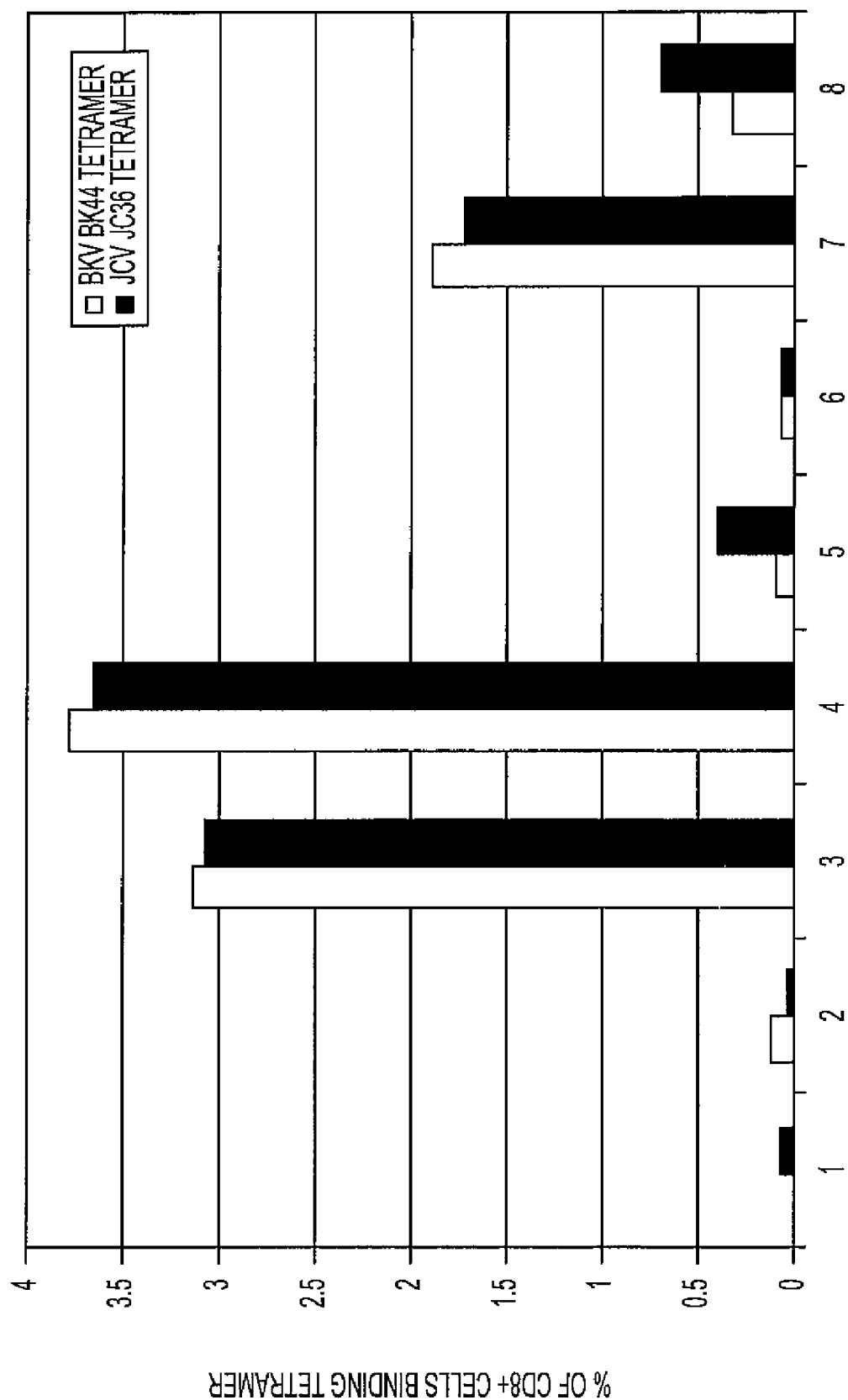

FIG. 18 is a bar graph summarizing the data from analyses of the type illustrated in FIGS. 16 and 17 on PBMC from 8 healthy normal HLA-A*02 donors.

Figure 19:
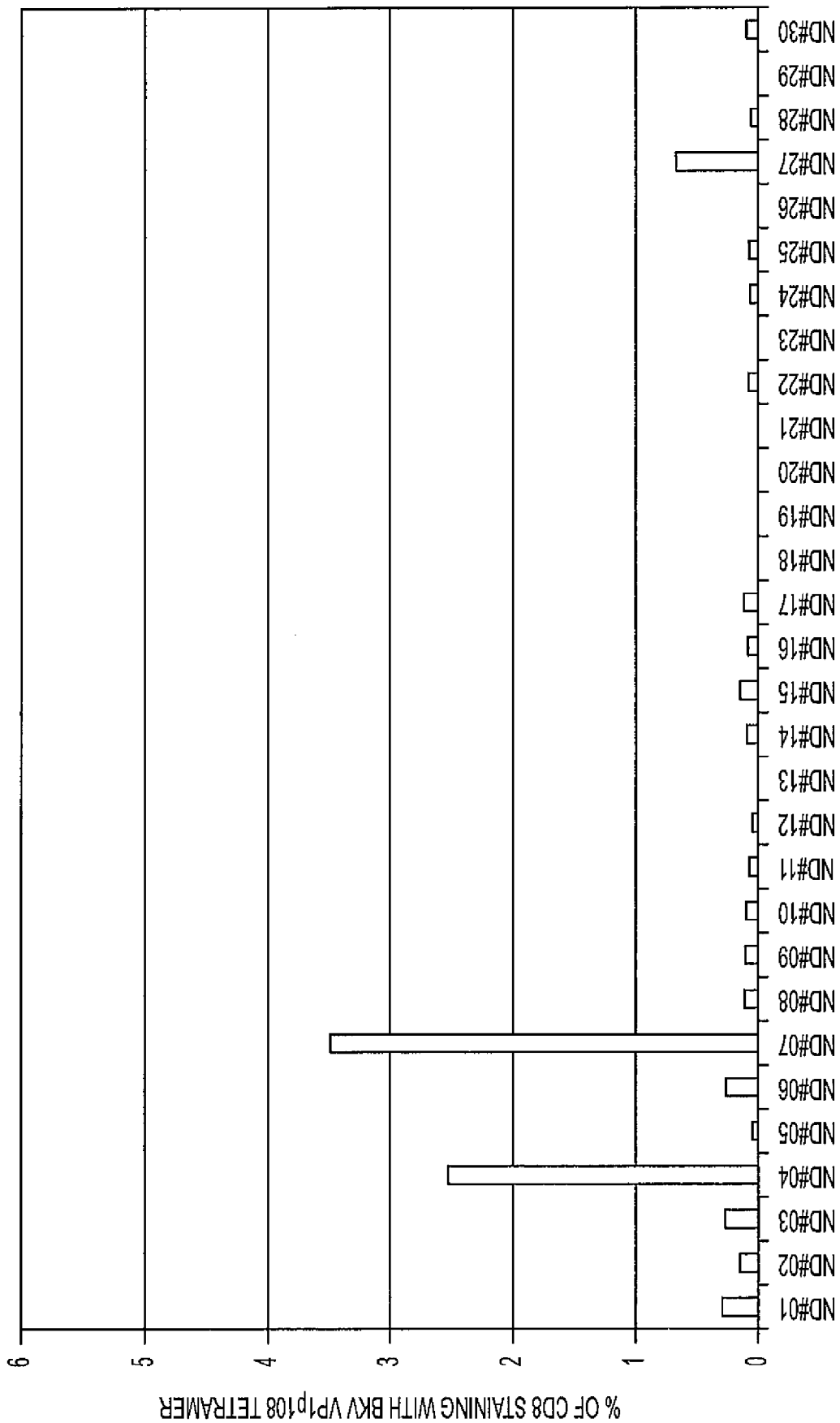

FIG. 19 provides flow cytometry staining results after in vitro stimulation with BK108 peptide, using BK108 tetramer reagent.

Figure 20:
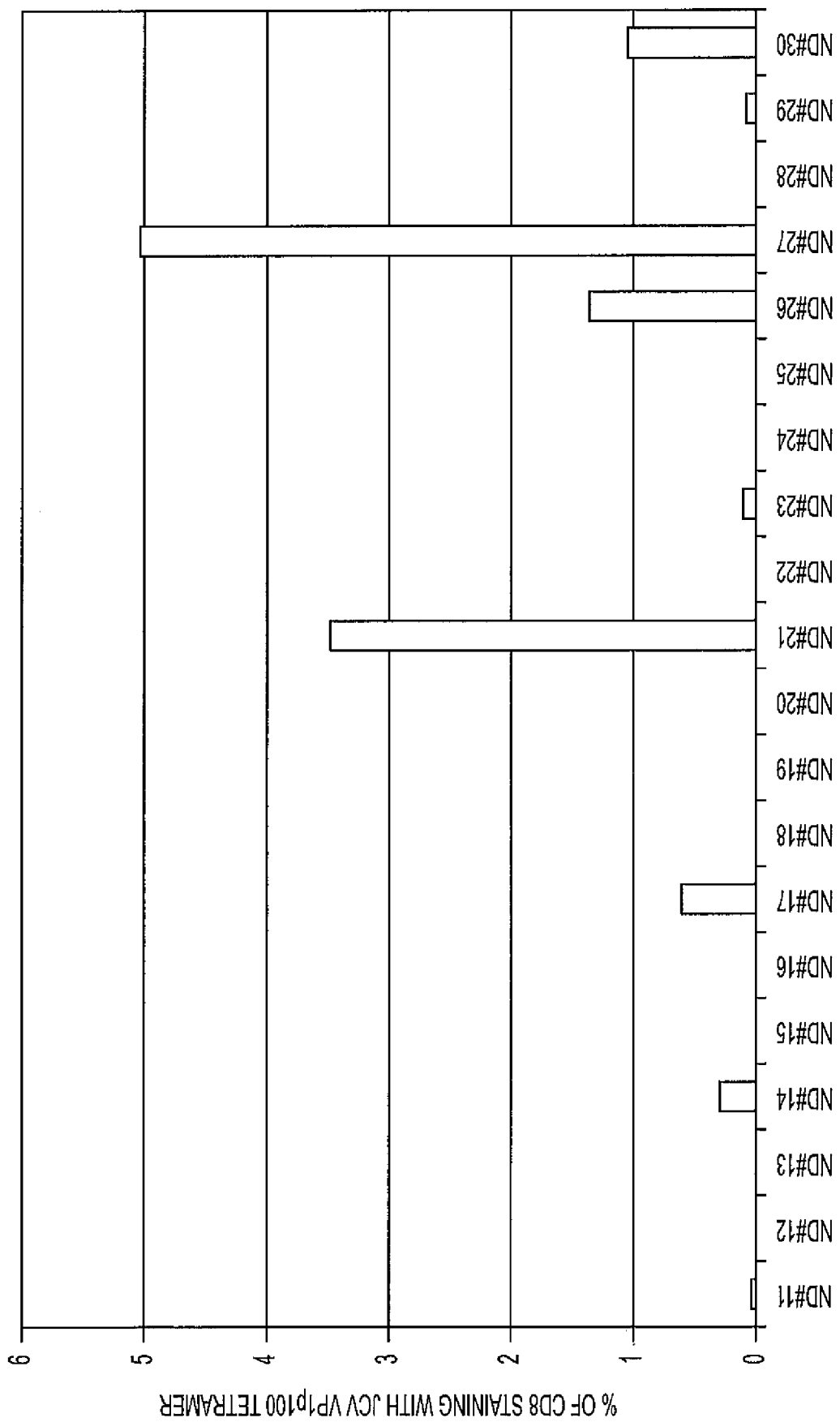

FIG. 20 provides flow cytometry staining results after in vitro stimulation with JC100 peptide, using JC100 tetramer reagent.

Figure 21:
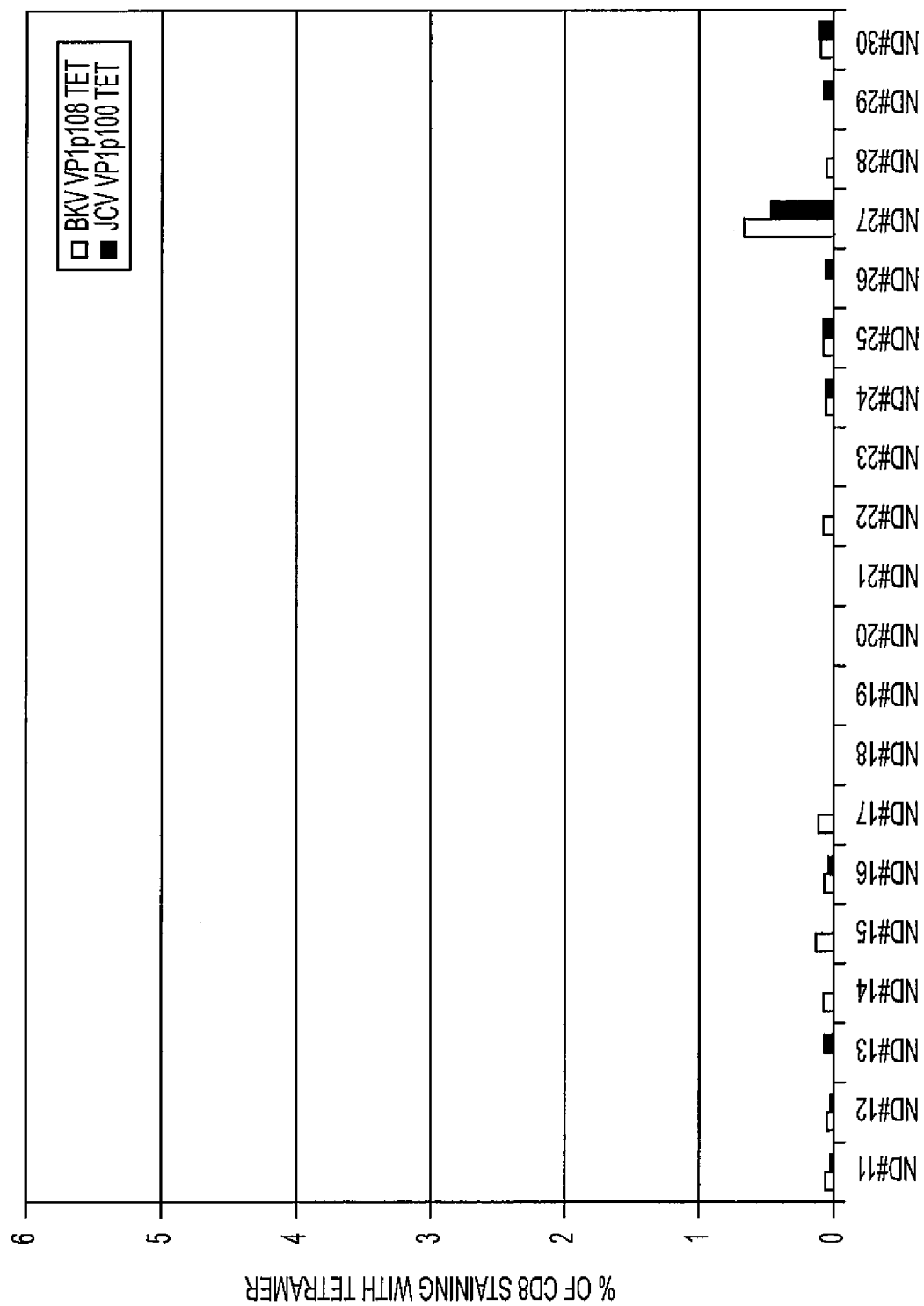

FIG. 21 provides flow cytometry double-staining results after in vitro stimulation with BK108 peptide, using both BK108 and JC100 tetramer reagents.

Figure 22:
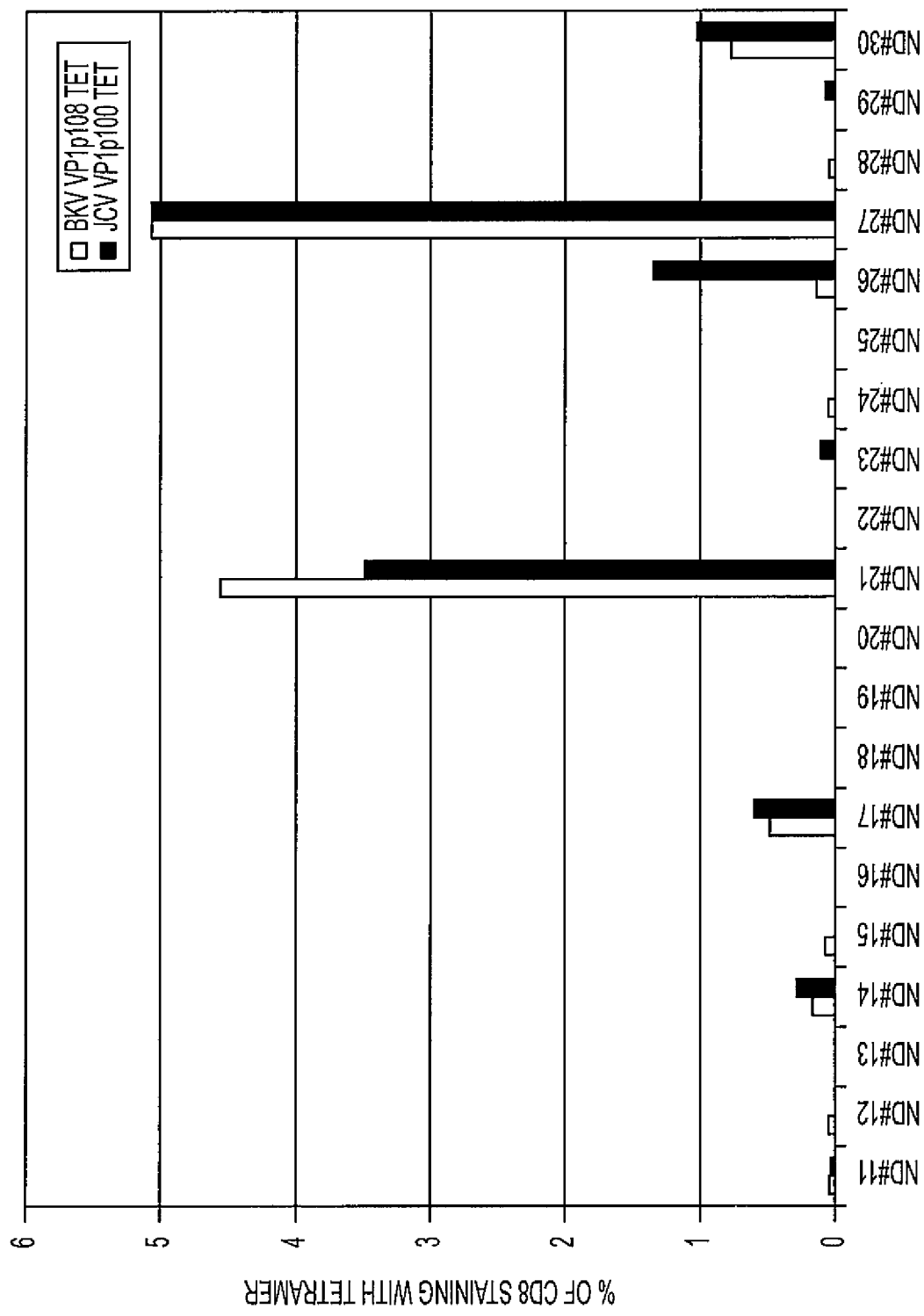

FIG. 22 provides flow cytometry double-staining results after in vitro stimulation with JC100 peptide, using both BK108 and JC100 tetramer reagent.

DETAILED DESCRIPTION OF THE PREFERRED EMBODIMENTS

The BK virus sequences LLMWEAVTV (SEQ ID NO:1; referred to herein as "BK108") and AITEVECFL (SEQ ID NO:5; referred to herein as "BK44") have been identified as immunodominant epitopes within the VP1 polypeptide of BK virus. These epitopes are restricted by HLA-A2 and are recognized by cytotoxic T lymphocytes (CTL) both in transgenic mice immunized with recombinant vaccinia virus and in humans naturally infected with BKV. In addition, CTL specific for these BKV epitopes can cross-recognize antigen presenting cells displaying the JC virus and SV40 homologs of the epitope. See Table I below for related sequences.

TABLE I

Polyomavirus Epitope Peptides.

| Virus | Name | Sequence | SEQ ID NO |
|---|---|---|---|
| BKV | BK108 | LLMWEAVTV | 1 |
| BKV | BK107 | NLLMWEAVTV | 2 |

TABLE I-continued

Polyomavirus Epitope Peptides.

| Virus | Name | Sequence | SEQ ID NO |
|---|---|---|---|
| JCV | JC100 | ILMWEAVTL | 3 |
| SV40 | SV108 | ILMWEAVTV | 4 |
| BKV | BK44 | AITEVECFL | 5 |
| JCV | JC36 | SITEVECFL | 6 |
| SV40 | SV44 | SFTEVECFL | 7 |

BK virus is a clinically important polyomavirus for which no antigenic epitopes were previously known. The BK108 and BK44 peptides are nine amino acids in length, and therefore correspond to the presumptive length of a minimal antigenic sequence. Using the BK108 and BK44 sequences, one can prepare specific probes, reagents and cells such as, for example, peptides containing the sequence or tetramer reagents folded with the sequence to track CTL specific for polyomavirus in human patients, for diagnostic or monitoring purposes, or antigen presenting cells or peptide vaccines for treatment and prophylaxis of polyomavirus-related disease. Tetramer reagents are described in Bieganowska et al., *J. Immunol.* 162:1765-1771, 1999 and Lebowitz et al., *Cell Immunol.* 192:175-184, 1999, the disclosures of which are hereby incorporated by reference.

CTL that recognize BK108 or BK44 can be protective against BKV or other polyomaviruses, for example the human JC virus and the simian virus SV40, both of which can infect humans and cause disease. Clinical BKV-related disease includes, but is not limited to, polyomavirus-associated nephropathy, hemorrhagic cystitis and prostate neoplasm. Many of these conditions have been associated with immunosuppression or related conditions. Patient populations who may take particular advantage of the present invention include, but are not limited to, kidney transplant patients, hematopoietic stem cell transplant patients, AIDS patients, prostate cancer patients and polyomavirus-negative persons. Any solid organ transplant patient or immunosuppressed person also may advantageously be treated with compounds comprising BK108 and/or BK44. BK108 and BK44 therefore can be useful as vaccines, for prophylaxis or treatment of infection with these polyomaviruses. Passive or active immunotherapy using cells presenting the BK108 and/or BK44 peptides can be useful in any patient infected with or at risk for infection by polyomaviruses. Thus, BK108 and BK44 form the basis for a peptide-based vaccine against polyomavirus. The peptides also are useful to expand polyomavirus-specific CTL for administration as adoptive T cell immunotherapy against polyomavirus.

In the studies reported here, immunization of transgenic mice that model the human immune system with rMVA expressing BKV VP1 produced CTL that recognize BK108 (LLMWEAVTV; SEQ ID NO:1) and cross-recognize the JCV VP1 homolog sequence JC100 (ILMWEAVTL; SEQ ID NO:3), as well as CTL that recognize BK44 (AITEVECFL; SEQ ID NO:5) and cross-recognize JC36 (SITEVECFL; SEQ ID NO:6). In addition, healthy BKV-seropositive HLA-A2 individuals and a kidney transplant recipient patient were shown to harbor low frequencies of CTL precursors that can be expanded by stimulation with BK108, JC100 or BK44 peptide into functional CTL that recognize both the relevant epitope and the BKV or JCV homolog sequence. The significantly higher levels of BKV/JCV VP1-specific CD8+ T cells seen in one of the two kidney transplant recipients tested, compared to the ten normal donors examined, suggests that the documented BKV reactivation in this individual drove expansion of CTL precursors specifically recognizing this epitope.

Du Pasquier et al. identified the JC100 and JC36 epitope sequences using a computer-based epitope prediction method. Du Pasquier et al., *Brain* 127(9):1970-1978, 2004; Du Pasquier et al., *J. Virol.* 78:10206-10210, 2004; Koralnik et al., *J. Immunol.* 168:499-504, 2002; see also Koralnik et al., *J. Immunol.* 168:499-504, 2002. Using JC100 and JC36 epitope peptides and tetramer reagents incorporating the peptides, those investigators identified CTL recognizing these epitopes in HLA-A*02 HIV+ PML survivors and in healthy individuals for whom the BKV serostatus was not reported. Correlation of clinical PML status and the presence of CTL recognizing these epitopes demonstrated an association between these cells and early control of PML. Du Pasquier et al., *Brain* 127(9):1970-1978, 2004; Koralnik et al., *J. Immunol.* 168:499-504, 2002. However, the data presented here show that the JCV VP1p100 and JCV VP1p36 epitope peptides and tetramer reagents based on these peptides are not JCV-specific, since they cross-react with cells elicited in response to and recognizing the BKV homolog peptide. Cellular responses recognizing the JC100 or JC36 epitopes in previous studies therefore may have been the result of JCV infection, BKV infection or infection with both viruses.

Given that the previously studied cellular immune responses are reported to protect against PML (Du Pasquier et al., *J. Neurovirol.* 7:318-322, 2001; Du Pasquier et al., *Brain* 127(9):1970-1978, 2004; Koralnik et al., *J. Immunol.* 168: 499-504, 2002), prior BKV infection may cross-protect against JCV disease. The studies reported here suggest that at-risk populations for BKV and/or JCV disease, and for SV40, can be monitored using diagnostic reagents based on BK108 (SEQ ID NO:1) or on BK44 (SEQ ID NO:5). In addition, immuno-interventive therapies based on these peptides can be targeted against the polyomaviruses BKV, JCV and SV40.

Those of skill in the art are fully able to devise schemes and compositions for vaccination and/or immune system modification using the peptide of this invention, and these variations are contemplated for use with the present invention. The following description, therefore, is intended to provide guidance and not to be limiting in any way.

The peptide of the invention may be formulated as vaccines according to any suitable method. Naked peptide or lipidated peptide may be formulated in any pharmaceutically acceptable carrier known in the art. Preferred peptide vaccine compositions also comprise an adjuvant. DNA adjuvants are preferred for human use. The peptides may be formulated as fusions with other immunogenic peptides from the same or a different pathologic entity. Peptides may be synthesized as fusions of the BK108 or BK44 peptides with one or more T-helper epitope such as PADRE or certain known tetanus peptides. Spacer peptides also may comprise part of these fusions.

The peptides may be formulated for any suitable mode of administration, however subcutaneous, intradermal, intramuscular, mucosal (e.g., rectal, nasal, vaginal, etc.), intraperitoneal, transdermal or inhalant modes of administration are preferred. Those of skill in the art of pharmaceutical formulation are well aware of appropriate and suitable carriers, diluents, excipients and other ingredients which may be used to create formulations for these modes of administration, and any of these compounds and formulations are contemplated for use with the invention. For human administration of a peptide or peptide fusion composition, a first immunization of about 10 mg to about 10,000 mg or preferably about 25 to about 2500 mg peptide is appropriate, followed by one, two or more booster immunizations at intervals (about 2-6 weeks), if desired.

The invention also includes DNA vaccines that encode the BK108 and/or BK44 peptides. Such DNA vaccines and methods for their formulation are known in the art. Generally, such vaccines are administered to previously infected or uninfected patients, or in vitro to T cells, in the form of a polynucleotide. A suitable gene-transfer vector such as a plasmid or engineered virus vector (for example MVA) is prepared to contain and express DNA that encodes the peptide or a peptide fusion, under the control of one or more appropriate expression regulatory sequences. T cells transfected in vitro with the DNA based vaccine may be administered to persons as well. For DNA immunizations, the patient preferably is injected intramuscularly with about 0.1-5 mg endotoxin-free DNA diluted in sterile saline or any other suitable pharmaceutical carrier, according to known methods.

Cellular vaccines and antigen presenting cells incorporating the BK108 and/or BK44 peptides also form part of the invention. Such cells and cellular vaccines are antigen-presenting cells that have been treated in vitro to cause them to present the peptide, for example, by in vitro incubation with (50 μM) BK108 and/or BK44 peptide for about 1-4 hours, followed by washing. Alternatively, the cells may be infected with a transfer virus vector containing DNA that encodes the peptide(s). The DNA construct for DNA vaccines may consist of a mammalian expression vector such as pVAX (Invitrogen™) in which the DNA sequence of each of the peptides of interest are inserted in the multicloning site, separated by spacers. For production of cellular vaccines, the described DNA construct may be electroporated into appropriate cells such as autologous dendritic cells.

The person of skill is readily able to determine patients who will benefit from vaccination or immune system modification with respect to polyomaviruses. In general, any person at risk of infection (prophylactic vaccine), such as children, or any person at risk of polyomavirus reactivation and disease (treatment vaccine), such as solid organ or other transplant recipient patients or donors, AIDS patients, cancer patients or any immunosuppressed person is a suitable candidate for the compositions and methods of this invention.

An additional aspect of the invention relates to diagnostic reagents for detection of polyomavirus infections. The BK108 and BK44 peptides can stimulate CTL directly in vitro and therefore can be used in an assay to determine the degree of immunostimulation being caused by polyomaviruses such as BKV, JCV and SV40. The peptides also can be used to diagnose individuals who are infected with polyomavirus. For use as a diagnostic reagent, for example for the detection of active versus quiescent BKV or other polyomavirus infection, the BK108 and/or BK44 peptides (or antigen-presenting cells presenting the peptide(s)) are contacted in vitro with a patient sample containing T cells according to the methods described in the Examples. Expansion of T cell clones recognizing the peptide from the patient sample indicates the presence of BK108- or BK44-reactive CTL and therefore polyomavirus infection. Bissinger et al., *Exp. Hematol.* 30:1178-1184, 2002, the disclosures of which are hereby incorporated by reference, have described the use of an intra-cellular cytokine (ICC) assay to expand HCMV-specific CTL with IL-2 and feeder cell stimulation using an HCMV epitope peptides. Using this method, not only can the ICC assay determine whether the subject is reactive to a particular peptide, but cells reacting to the peptide can be isolated and expanded to be used for adoptive immunotherapy.

Alternatively, tetramer reagents and the like, which are known in the art (see U.S. Pat. No. 5,734,023, the disclosures of which are hereby incorporated by reference) may be constructed from the peptides of the invention to detect T cells that recognize BK108 or BK44. See Lacey et al. *Transplantation* 74:722-732, 2002, the disclosures of which are hereby incorporated by reference, and Example 4 for appropriate methods. Tetramer reagent-positive cells may be transferred into the recipient in whom expansion is desired, to protect against polyomavirus-related disease.

EXAMPLES

Example 1

Identification of HLA-A*02-Restricted Epitopes of BKV VP1

Sequences with the motif characteristics of T-cell epitopes were identified within the open reading frames encoding the BKV VP1 major capsid polypeptide using computer-based algorithms that predict 9- or 10-mer amino acid sequences likely to be generated by proteasomal cleavage and to bind to HLA-A*02. The SYFPEITHI™, BIMAS™, SVMHC™ and FRAGPREDICT™ algorithms were used to select the panel of 6 candidate epitopes shown in Table II, below.

TABLE II

Predicted HLA-A2 Restricted Epitopes from BKV VP1.

| Peptide Name | VP1 Position | Sequence | SEQ ID NO: |
|---|---|---|---|
| BK26 | 26-35 | KLLIKGGVEV | 8 |
| BK27a | 27-36 | LLIKGGVEVL | 10 |
| BK27b | 27-35 | LLIKGGVEV | 9 |
| BK108 | 108-116 | LLMWEAVTV | 1 |
| BK107 | 107-116 | NLLMWEAVTV | 2 |
| BK109 | 109-118 | LMWEAVTVQT | 11 |

Peptides were synthesized using standard FMOC protocols using a Symphony Quartet™ peptide synthesizer and purified to greater than 95% purity by HPLC. The identity of the peptides was confirmed by MALDI TOF mass spectrometric analysis using a Kompact Probe™ mass spectrometer. These peptides then were tested for their ability to bind HLA-A*02 and stabilize its expression on the surface of TAP-deficient T2 cells. Levels of surface HLA-A2 were measured by staining peptide-pulsed T2 cells with a fluorescent-labeled antibody to HLA-A2 followed by flow cytometric analysis. Five of the six VP1 peptides clearly showed positive HLA-A2 binding as measured by an increase in relative fluorescence intensity on the surface of the cells.

Figure 1:
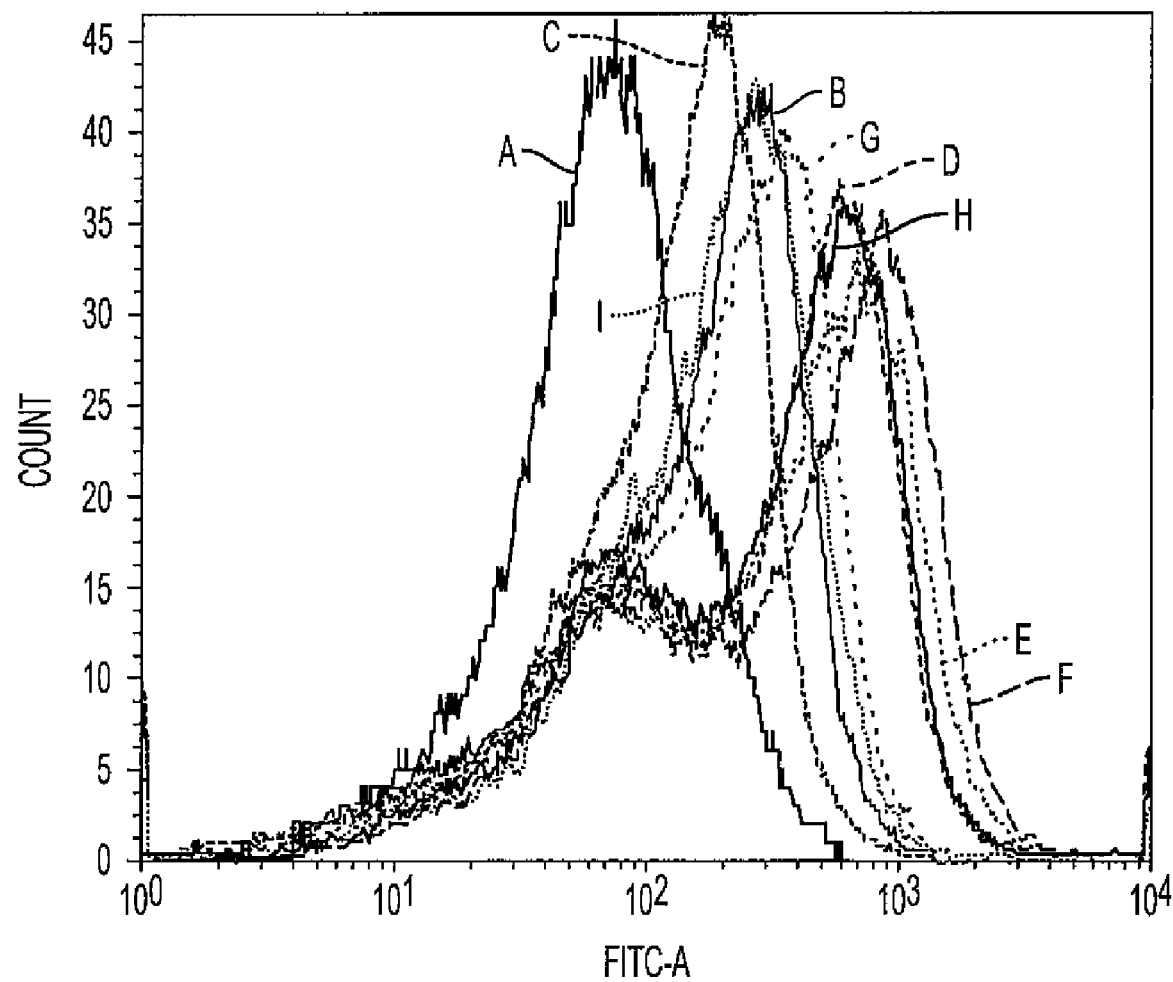

See FIG. 1 for results of a representative cell-binding assay. The degree of binding to T2 cells in culture is indicated by the degree of displacement (to the right) of the overlaid histograms on the X-axis of the Figure, which indicates increased fluorescence, corresponding to higher levels of stabilized peptide-HLA complex on the surface of the T2 cells. Peptides BK108, BK27b and BK107 demonstrated the highest binding function, comparable to a positive control HLA-A2-binding peptide corresponding to a well-defined immunodominant epitope from the human cytomegalovirus pp65 polypeptide (NLVPMVATV; SEQ ID NO:14).

Example 2

In Vivo Immunogenicity Testing in Transgenic Mice

Peptides BK26, BK27b, BK108, and BK107 were used to immunize HHD-II transgenic mice, with a CpG-rich oligodeoxynucleotide and PADRE T-helper peptide in incomplete Freund's adjuvant. These HHD-II mice have a humanized immune system and are well-recognized to predict immune responses in humans. The mice express a transgenic monochain histocompatability class I molecule in which the C terminus of the human β2m is covalently linked to the N terminus of a chimeric heavy chain (HLA-A*0201-α1, -α2, H-2D$^b$-α3-transmembrane, and intracytoplasmic domains). See Firat et al., *Eur. J. Immunol.* 29:3112-3121, 1999, the disclosures of which are hereby incorporated by reference. Fourteen days after immunization, the mice were sacrificed, the spleen removed, and parallel in vitro stimulation cultures were set up using each of the four peptides above.

In vitro stimulation of PBMC was performed as follows. Cryopreserved PBMC were cultured in 24-well tissue culture plates at a density of 3.5 million cells/mL in RPMI 10 containing 1 µg/mL of either BK108 (SEQ ID NO:1) or JC100 (SEQ ID NO:3) at 37° C. in a $CO_2$-gassed incubator. After 3 days of culture, recombinant human IL-2 (rIL-2) was added to 30 units/mL. Every two days thereafter, 50% of the culture medium was removed and replaced by fresh medium containing rIL-2. Incubation was continued for 11-14 days before flow analysis.

Figure 2:
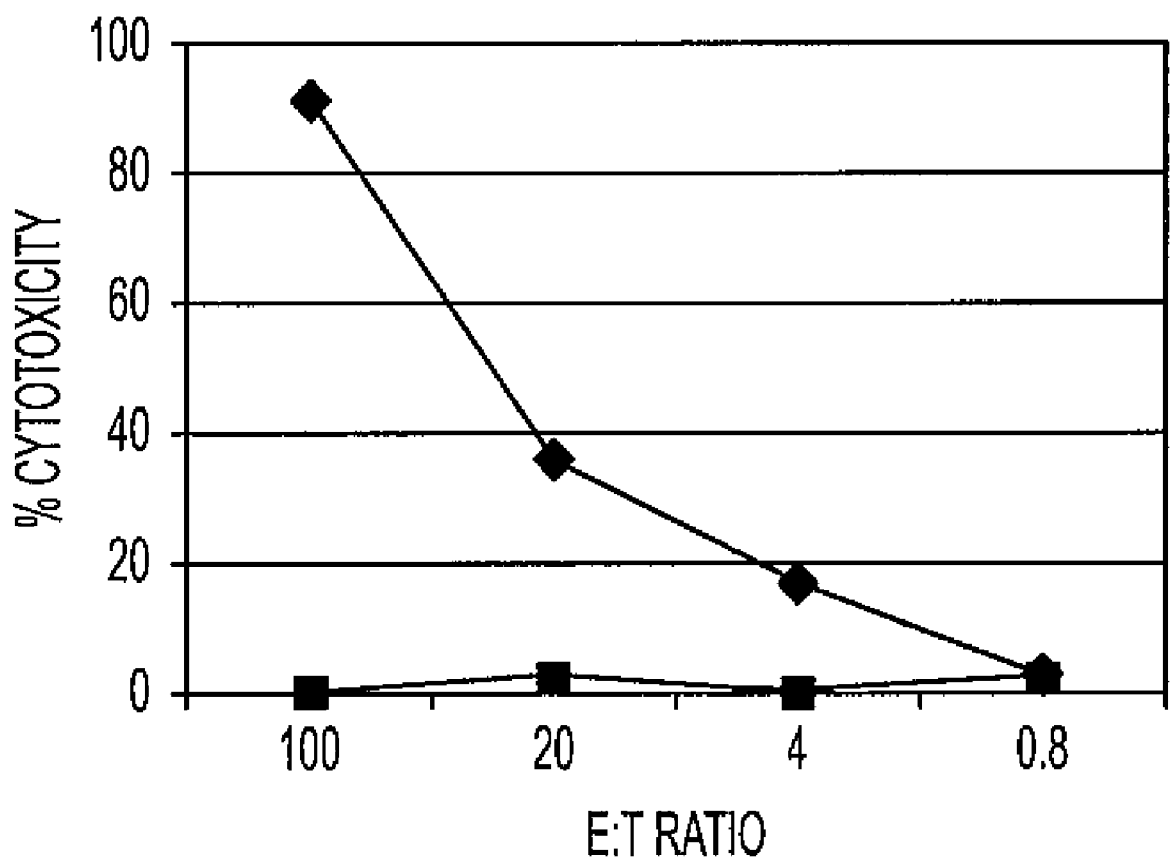
Figure 3A:
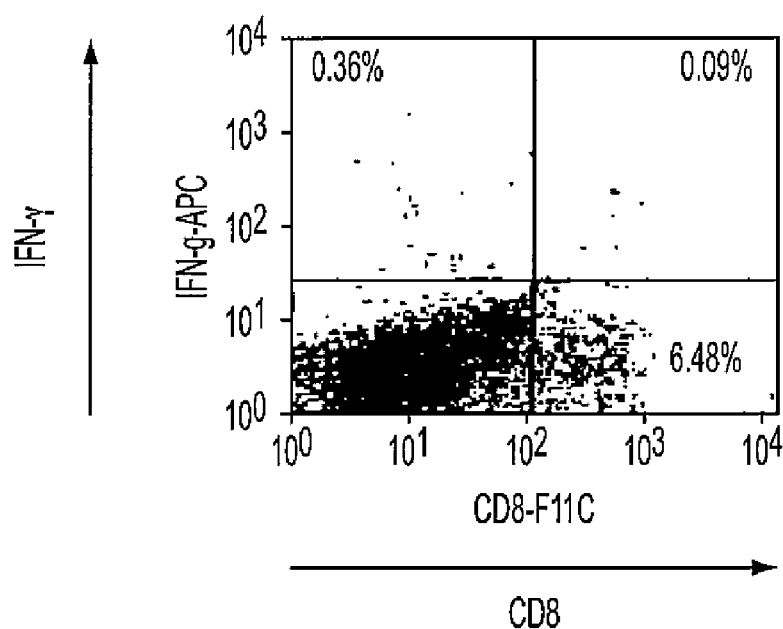
Figure 3B:
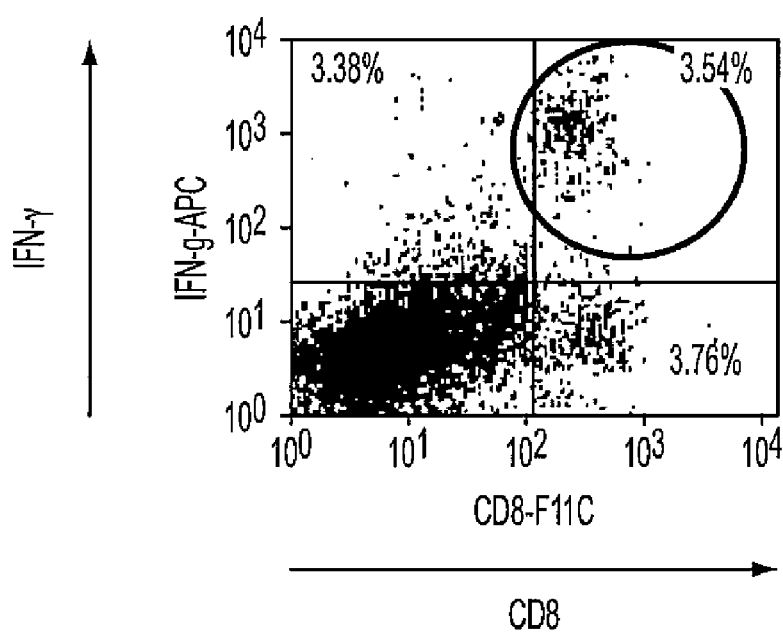

The stimulated cultures were tested for cytotoxicity against antigen-presenting Jurkat cells loaded with the peptide with which they were stimulated. Flow cytometric intracellular cytokine (ICC) assays also were used to test the stimulated cultures for the presence of CD8$^+$ T cells that produce IFN-γ in response to stimulation by the cognate peptide. See FIGS. 2 and 3. The data indicate that mice immunized with BK108 (with CpG DNA, PADRE and incomplete Freund's adjuvant) responded by producing cytotoxic T lymphocytes that specifically recognize this BKV VP1 epitope.

Example 3

In Vivo Processing of VP1 Generates the Peptide Epitope, BK108

A transgenic murine model was used to test whether the peptides that showed positive HLA-A2 binding in vitro were generated by in vivo cellular processing and displayed on the surface of antigen-presenting cells. A recombinant Modified Ankara Virus (MVA) was constructed to express the BKV VP1 polypeptide as follows: nucleotide sequences corresponding to the BKV antigen and VP1 open reading frame sequences of interest were cloned by PCR amplification using pBKV (33-1; ATCC #45024) as a template. The amplification products were cloned into pCR2.1, and verified by nucleotide sequencing before re-cloning into the recombination vector pLW22-1. Generation and selection of rMVAs was performed using previously described methods. See Wang et al., *J. Virol.* 78:3965-3976, 2004. Verification of expression was done by immunostaining of BHK monolayers infected with the rMVAs using an anti-polyomavirus antibody (Novocastra™).

The MVA recombinant expressing the VP1 polypeptide was used to immunize transgenic HHD-II mice (knockout for murine class I alleles and expressing a chimeric HLA-A2 and Kb molecule) with no adjuvant or booster immunizations. HHDII mice (8-12 weeks old) were immunized intraperitoneally with 3 to 5×10⁷ pfu of rMVA expressing BKV VP1. Expression of the BKV polypeptide was verified by immunostaining of infected BHK monolayers. The animals were sacrificed after 2 weeks and the spleens retrieved. Single-cell splenocyte suspensions were prepared by passing the cells through a 70 μm cell strainer using the plunger from a sterile 1 mL syringe. Parallel in vitro stimulation cultures were set up using each of the four peptides BK26, BK27b, BK108 and BK107. Splenocytes were subjected to one round of in vitro expansion according to the methods of La Rosa et al., *Blood* 100:3681-3689, 2002. Briefly, the splenocytes from immunized animals were co-cultured with peptide-loaded lipopolysaccharide (LPS) blasts in complete IVS medium (RPMI medium supplemented with 10% FCS, with glutamine, penicillin and streptomycin) at a ratio of 3:1 for 7 days, with the addition of 10% rat T-stim™. At the end of this in vitro expansion step, the splenocytes were tested for their ability to lyse naïve syngeneic splenocytes pulsed with the cognate peptides (cytotoxicity) and for their ability to produce IFN-γ on stimulation with these same peptides in ICC assays.

Cytolytic activity of effector cell populations was determined using a 4-hour chromium release assay (CRA) following one in vitro stimulation according to the methods of Daftarian et al., *J. Immunol.* 171:4028-4039, 2003 and La Rosa et al., *Blood* 97:1776-1786, 2001. The target cells were Jurkat A2.1 cells pulsed with 10 μM of the relevant or control HIV peptides or infected for 2-3 hours with 15 MOI of rMVA expressing BKV T antigen, VP1 or control polypeptides. For the assays, the Jurkat A2.1 target cells were loaded with 200 μCi of Na$^{51}$CrO$_4^-$ for 1 hour in a 37° C. water bath and further processed as described in La Rosa et al., *Blood* 97:1776-1786, 2001, the disclosures of which are hereby incorporated by reference. Experimental evaluations were performed in triplicate.

For ICC assays, splenocytes, after 1 week in vitro stimulation, were tested for IFN-γ production after stimulation overnight with 5 μM BK108 peptide or control. The following day, brefeldin A was added to all the cultures and incubation continued for 4 hours. The cells then were washed with 3 mL PBS containing 0.5% BSA before labeling for 20 minutes at 4° C. with FITC-conjugated murine CD8-specific antibody. The cells then were washed again with PBS containing 0.5% BSA, permeabilized with Cytofix/Cytoperm™ and labeled with APC- or PE-conjugated anti-IFN-γ antibody 30 minutes at 4° C. The cells then were washed and analyzed by flow cytometry.

Figure 4:
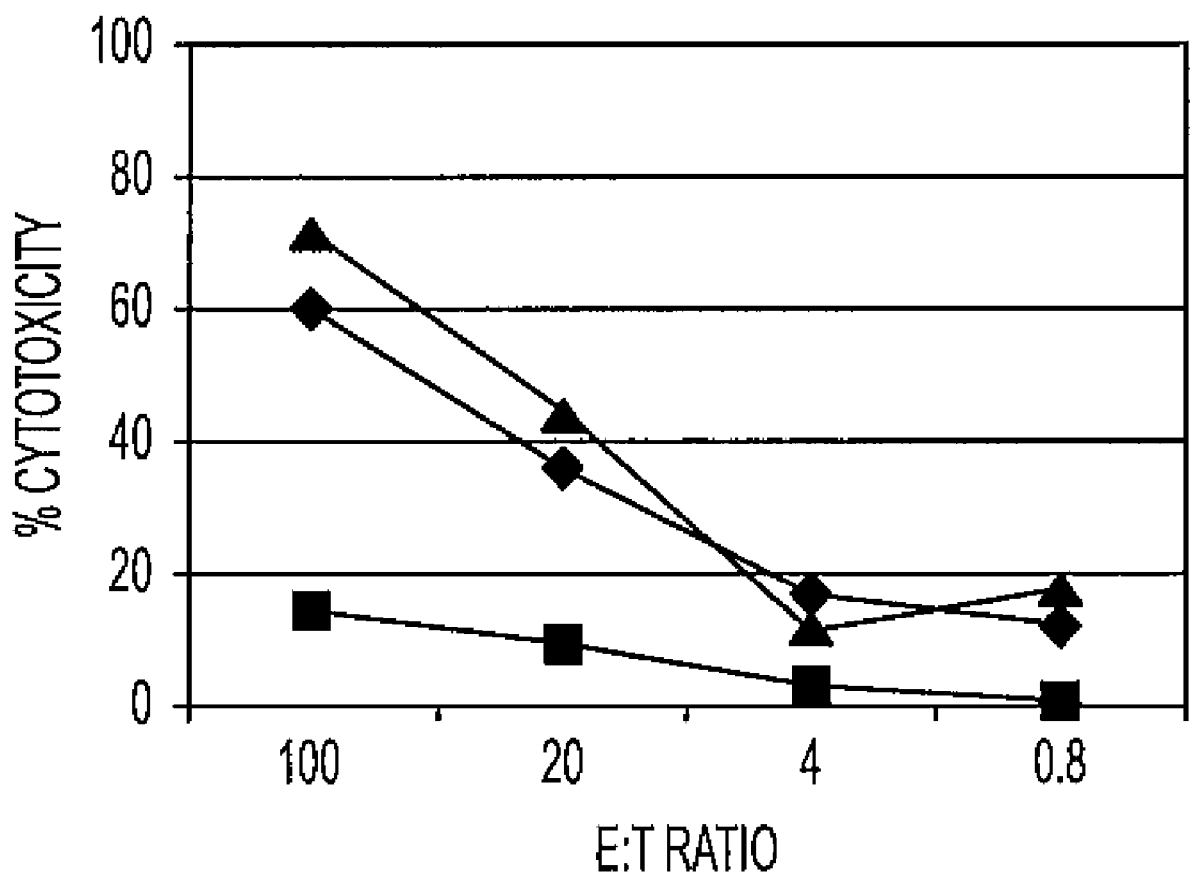
Figure 5A:
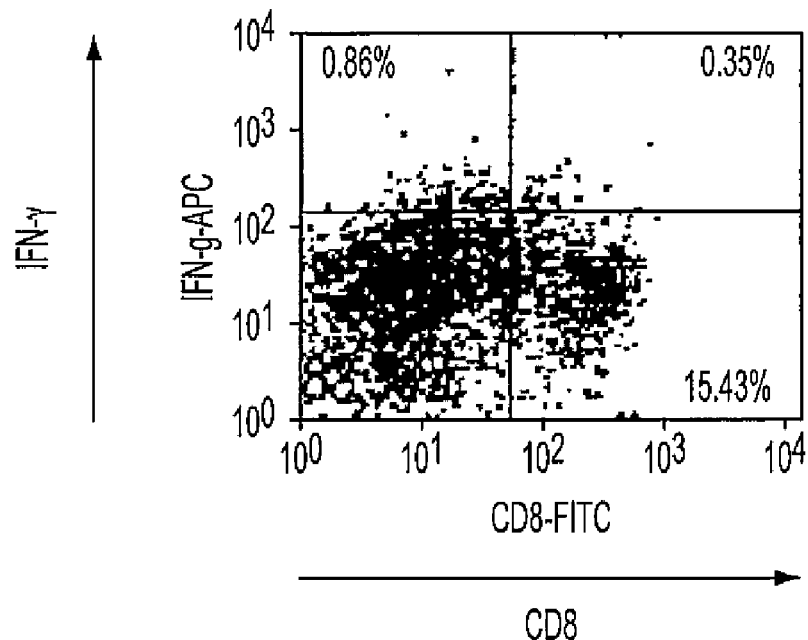
Figure 5B:
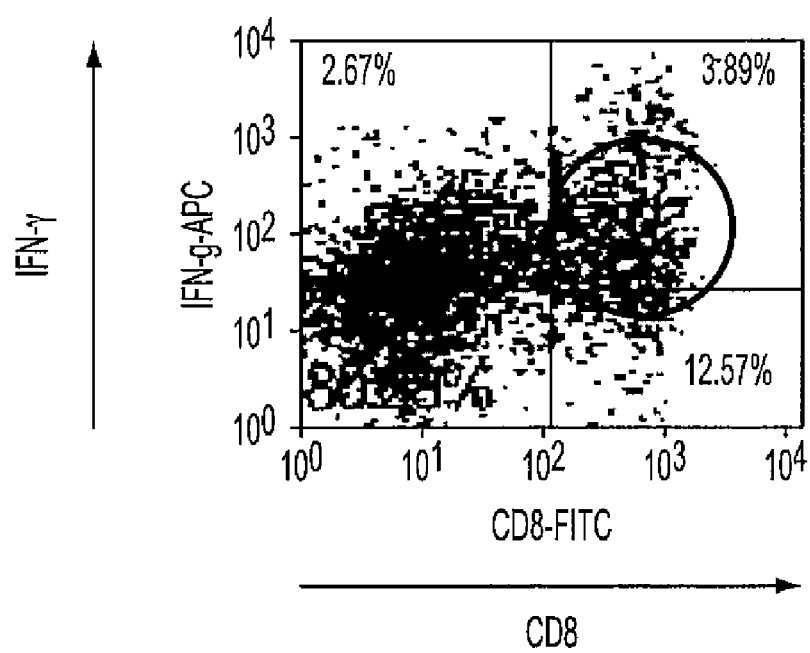

Results of the cytotoxicity and ICC assays are presented in FIGS. 4 and 5. FIG. 4 shows the percent cytotoxicity of targets loaded with two different preparations of BK108 peptide (diamonds and triangles) or with an irrelevant control peptide (squares) by splenocytes immunized in vivo with BK108. FIG. 5 provides data from ICC assays performed on cells with control HIV peptide (FIG. 5A) and with BK108 peptide (FIG. 5B). A significantly larger proportion of BK108-stimulated cells (3.89%) responded compared to control cells stimulated with an irrelevant HIV peptide (0.35%). Cells responding to stimulation with IFN-γ production are circled in FIG. 5B. Of the tested BKV peptides, only peptides BK108 (LLM-WEAVTV; SEQ ID NO:1) and BK107 (NLLMWEAVTV; SEQ ID NO:2) yielded positive results. Therefore, in the immunized mice, VP1 polypeptide, expressed by the MVA recombinant, was processed within mouse cells, in vivo, (1) to yield the antigenic epitope corresponding to peptide BK108, presented on the surface of antigen presenting cells and (2) to induce the generation of CTL recognizing this same epitope.

The JCV homolog (JC100; ILMWEAVTL; SEQ ID NO:3), which differs at the C terminal and N terminal positions from the BKV VP1 sequence, has been described as a functional HLA-A*02-restricted cellular epitope in humans. See Du Pasquier et al., *J. Virol.* 77:11918-11926, 2003; Du Pasquier et al., *J. Virol.* 78:10206-10210, 2004; Koralnik et al., *J. Immunol.* 168:499-504, 2002. The above experiments were repeated using BK108-immunized splenocytes assayed for their ability to recognize target cells presenting this JCV homolog sequence.

Figure 7A:
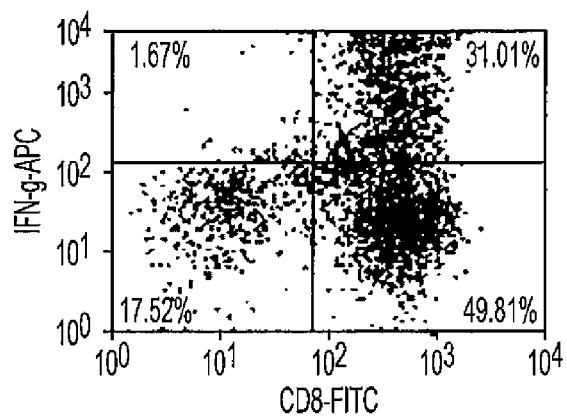
Figure 7B:
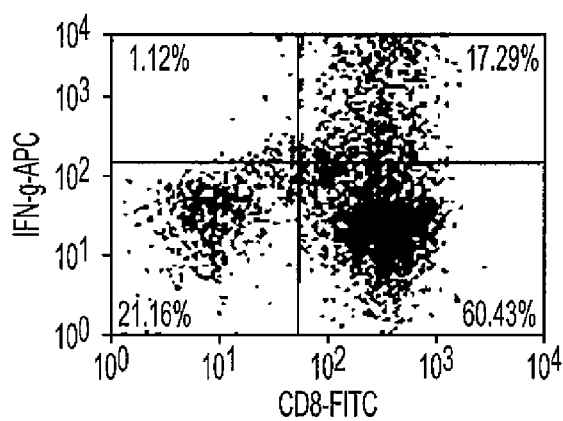
Figure 7C:
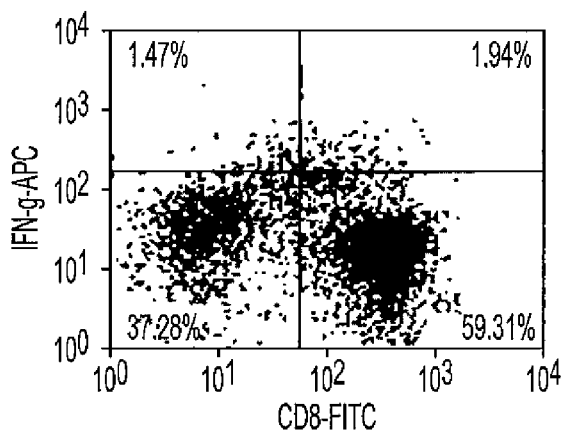
Figure 8A:
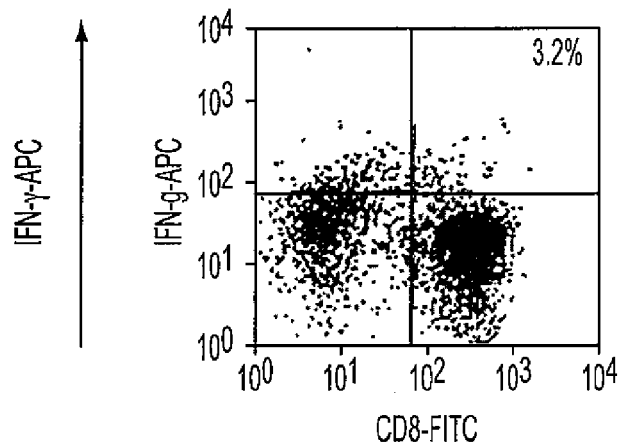
Figure 8B:
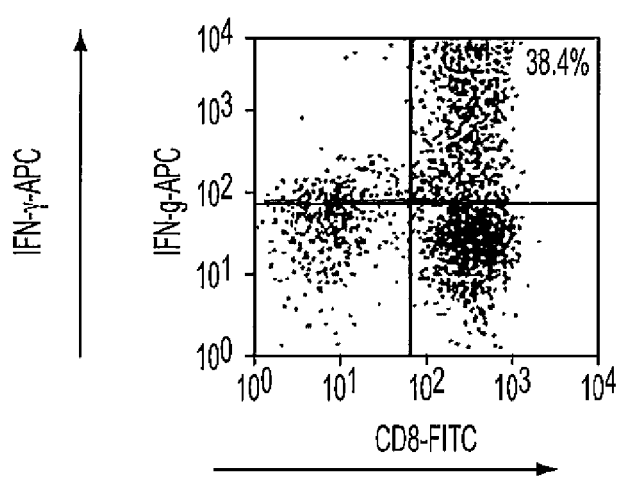
Figure 8C:
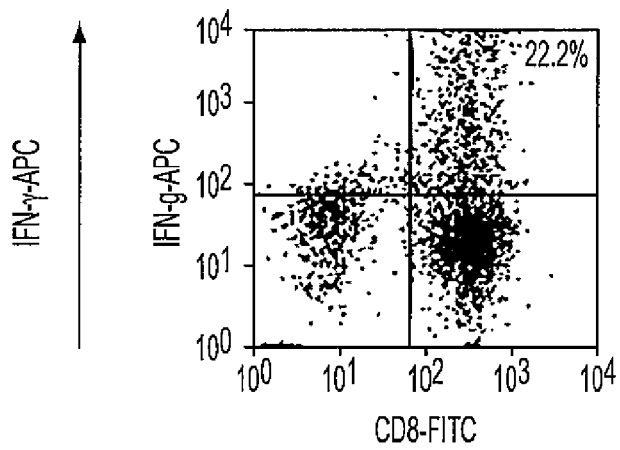

The peptide, JC100, was synthesized and compared with the BK108 peptide in cytotoxicity and ICC assays using the murine effectors elicited by immunization with rMVA-BKV VP1 and expanded by stimulation with BK108, as described above. Transgenic HHD-II mice (4 per group) were immunized intraperitoneally with 3×10⁷ plaque forming units of rMVA-BKV VP1. Two weeks after immunization, the mice were sacrificed, spleens harvested, and the splenocytes cocultivated with syngeneic irradiated peptide-pulsed naïve mouse splenocytes. After 1 week of in vitro stimulation, the cultured cells were tested for specific cytotoxicity versus A2-Jurkat cells pulsed with peptides and in ICC assays for IFN-γ production on peptide stimulation. Results show that the transgenic murine CTL elicited by immunization with the BKV epitope recognized both the BKV and JCV VP1 homologs, with only a somewhat higher affinity for the BKV sequence. See FIGS. 6-8.

Figure 6:
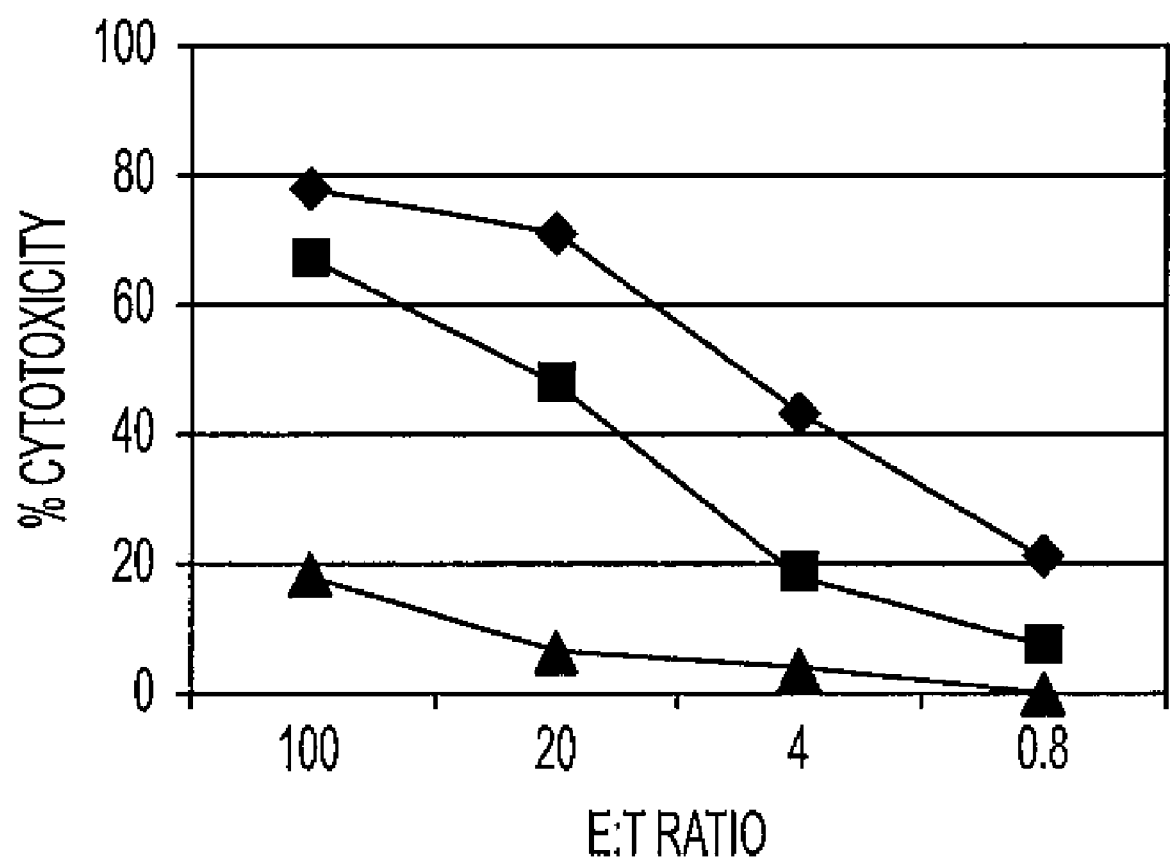

FIG. 6 shows killing by BK108-immune splenocytes of targets presenting BK108 (diamonds), JC100 (squares) or control HIV peptide (triangles). In two separate experiments, 31.01% (FIG. 7A) or 38.4% (FIG. 8B) of the cells produced IFN-γ in response to BK108, while 17.29% (FIG. 7B) or 22.2% (FIG. 8C) of the cells produced IFN-γ in response to JC100, compared to 1.94% (FIG. 7C) or 3.2% (FIG. 8A) for the control peptide. Thus, protective immune responses against the BKV epitope can protect against JCV. In addition, this peptide should protect against SV40, which has an epitope previously identified as ILMWEAVTV (SEQ ID NO:4), because this sequence differs by only one amino acid from each of the BKV and JCV sequences (see Table I). Since most adult humans are infected with both JCV and BKV, and SV40 also is highly prevalent, this multifactorial protection can be important both for prophylactic vaccination and for treatment, particularly in immunosuppressed patients.

Example 4

Identification of BKV VP1 Epitope-Specific CD8⁺ T Cells in Humans

To confirm that the cross-reactivity between BKV and JCV VP1 epitopes seen in the transgenic mouse model also exists in humans, a HLA-A*0201 tetramer reagent incorporating the BK108 epitope peptide was prepared and conjugated to the fluorochrome allophycocyanin (APC) using known methods. See Krausa et al., *Tissue Antigens* 47:237-244, 1996, the disclosures of which are hereby incorporated by reference. This tetramer reagent (termed BK108tet-APC) was used to screen PBMC samples from ten randomly-selected healthy donors and two kidney transplant recipients, each expressing the HLA-A*0201 phenotype.

HLA typing for all donors was performed by PCR according to known methods. See Krausa and Browning, *Tissue Antigens* 47:237-244, 1996. PBMC from ten healthy normal HLA-A*02 haplotype donors and from two kidney transplant recipients (designated KTx#04 and KTx#07) were collected. KTx#04 had documented BKV viremia and viruria, but no biopsy evidence of BKVN; KTx#07 had documented viruria, but no viremia or biopsy evidence of BKVN. The PBMC were stimulated once in culture with BK108 in the presence of 30 U/mL rIL2 (added at day three). After a 14-day incubation period, the cultures were stained with FITC-conjugated antibody to CD8 and with BK108tet-APC reagent for flow cytometry analysis according to the methods of Lacey et al. *Transplantation* 74:722-732, 2002. Results were obtained using gates set on lymphocytes by forward versus side scatter.

The cytometry results are shown in FIG. 9A-9L. See also the key in Table III, below. The data indicated that after this in vitro expansion, PBMC from two of the ten healthy donors had obvious populations of $CD8^+$ T lymphocytes that bound the BK108 tetramer reagent (see 9D and 9G). Tetramer reagent-binding populations are circled for emphasis, and their frequencies indicated as a percentage of $CD8^+$ T-lymphocytes. Two more individuals also may have had very small tetramer-binding populations that were difficult to resolve from the assay background (see, for example, 9B). Labeling of unstimulated PBMC from the positive healthy donors with BK108tet-APC did not detect any specific binding above background, indicating that the levels of CTL precursors in PBMC is below the detection limit of the tetramer-binding assay (approximately 0.05% of $CD8^+$ PBMC).

One of the two kidney transplant recipients tested harbored a very large population of BK108tet-APC binding cells after stimulation (see FIG. 9L). The frequency of these cells was ten-fold higher than seen in the two positive normal donors (24.9% of $CD8^+$ T cells after amplification versus 1.9% and 3.3%). These findings confirm the relevance of the findings in the well-accepted transgenic mouse model to humans.

TABLE III

Key to FIG. 9.

| Figure | Donor |
|---|---|
| 9A | normal 1 |
| 9B | normal 2 |
| 9C | normal 3 |
| 9D | normal 4 |
| 9E | normal 5 |
| 9F | normal 6 |
| 9G | normal 7 |
| 9H | normal 8 |
| 9I | normal 9 |
| 9J | normal 10 |
| 9K | KTx#04 |
| 9L | KTx#07 |

Example 5

Functionality and Specificity of BK108 Tetramer-Binding $CD8^+$ T Cells

A modified flow-based assay confirmed that $CD8^+$ T cells bound by the BK108 tetramer reagent were functional CTL that specifically recognized this epitope. This assay combined tetramer reagent staining, intracellular cytokine staining and measurement of mobilization of cytotoxic granules. See Betts et al., *J. Immunol. Meth.* 281:65-78, 2003; Betts et al., *J. Immunol.* 172:6407-6417, 2004; Wolint et al., *J. Exp. Med.* 199:925-936, 2004; Lacey et al., *J. Infect. Dis.* 191:977-984, 2005 for relevant methods. The disclosures of these references are hereby incorporated by reference.

In this type of assay, PBMC first are stained with a tetramer reagent for the antigenic peptide of interest, then stimulated for 4 hours in culture with the same peptide in the presence of co-stimulatory antibodies and fluorochrome labeled antibodies specific for the lysosome-associated membrane proteins LAMP-1 (CD107a) and LAMP-2 (CD107b), molecules that are present on the membranes of cytotoxic granules in these cells. Monensin also is added to the culture to inhibit secretion of cytokines and to neutralize the pH within the cytotoxic granules, avoiding quenching fluorescence of the fluorochrome conjugated to the anti-CD107a and anti-CD107b antibodies.

If the cells under study recognize the peptide, then during the incubation step engagement of the TCR by the peptide presented on the MHC—I complex of antigen presenting cells within the PBMC population causes (1) production of IFN-γ and (2) mobilization of the cytotoxic granules to the cell surface where they fuse with the plasma membrane. Cytotoxic granule fusion exposes the CD107a and CD107b markers to the exterior milieu, where they are labeled by the fluorochrome conjugated anti-CD107a and anti-CD107b antibodies. The cells are fixed, permeabilized, and stained with labeled antibodies specific for IFN-γ and CD8 for flow analysis. For additional discussion of the technical aspects of this flow-based functional assay see Betts et al., *J. Immunol. Meth.* 281:65-78, 2003, the disclosures of which are hereby incorporated by reference.

The combined ICC and CD107 mobilization/degranulation assays performed here essentially followed the methods described in Betts et al., *J. Immunol. Meth.* 281:65-78, 2003. Cells from BK108 in vitro stimulation cultures were washed once with RPMI 10 medium. Aliquots of 1 million cells were labeled with BK108 tetramer reagent in 100 μL of the same medium for 30 minutes at 37° C. One milliliter of RPMI 10 medium and FITC-conjugated antibodies specifically binding CD107a and CD107b (Pharmingen™) then were added to each aliquot, followed by 1 μg/mL each of co-stimulatory antibodies to CD28 and CD49d (Pharmingen™). Antigenic peptide corresponding to that incorporated in the tetramer reagent or irrelevant control peptides then were added to some of the tubes to a final concentration of 5 μM. Monensin (1 μL, GolgiStop™) was added to all the tubes, which then were incubated at 37° C. in a $CO_2$-gassed incubator for 5 hours. The cells then were washed with 3 mL PBS containing 0.5% BSA and labeled for 20 minutes at 4° C. with PerCP-conjugated antibody to CD8 (Pharmingen™). The cells then were washed again with PBS containing 0.5% BSA, permeabilized with Cytofix/Cytoperm™ and labeled with APC-conjugated antibody to IFN-γ for 30 minutes at 4° C.

The cells were washed a final time and resuspended in 0.5 mL sheath fluid (FACSFlow™, Becton Dickinson™) for flow analysis. A primary gate was set on lymphocytes using forward and side scatter, and a secondary gate was set on $CD8^+$ tetramer reagent-binding cells. At least 100,000 events were collected per sample. The percentage of $CD8^+$ tetramer reagent-binding lymphocytes expressing elevated surface CD107a/b and secreting IFN-γ was determined by reference to controls incubated with co-stimulatory antibodies to CD28 and CD49d but no peptides. In this assay, the expanded cell culture was labeled with BK108tet-APC and restimulated in culture for 4 hours with peptide in the presence of co-stimulatory antibodies, monensin and FITC-conjugated antibodies specific for CD107a and CD107b. After permeabilization and labeling with CyChrome™-conjugated antibody to CD8 and PE-conjugated antibody to IFN-γ, the cells were subjected to flow analysis.

Figure 10:
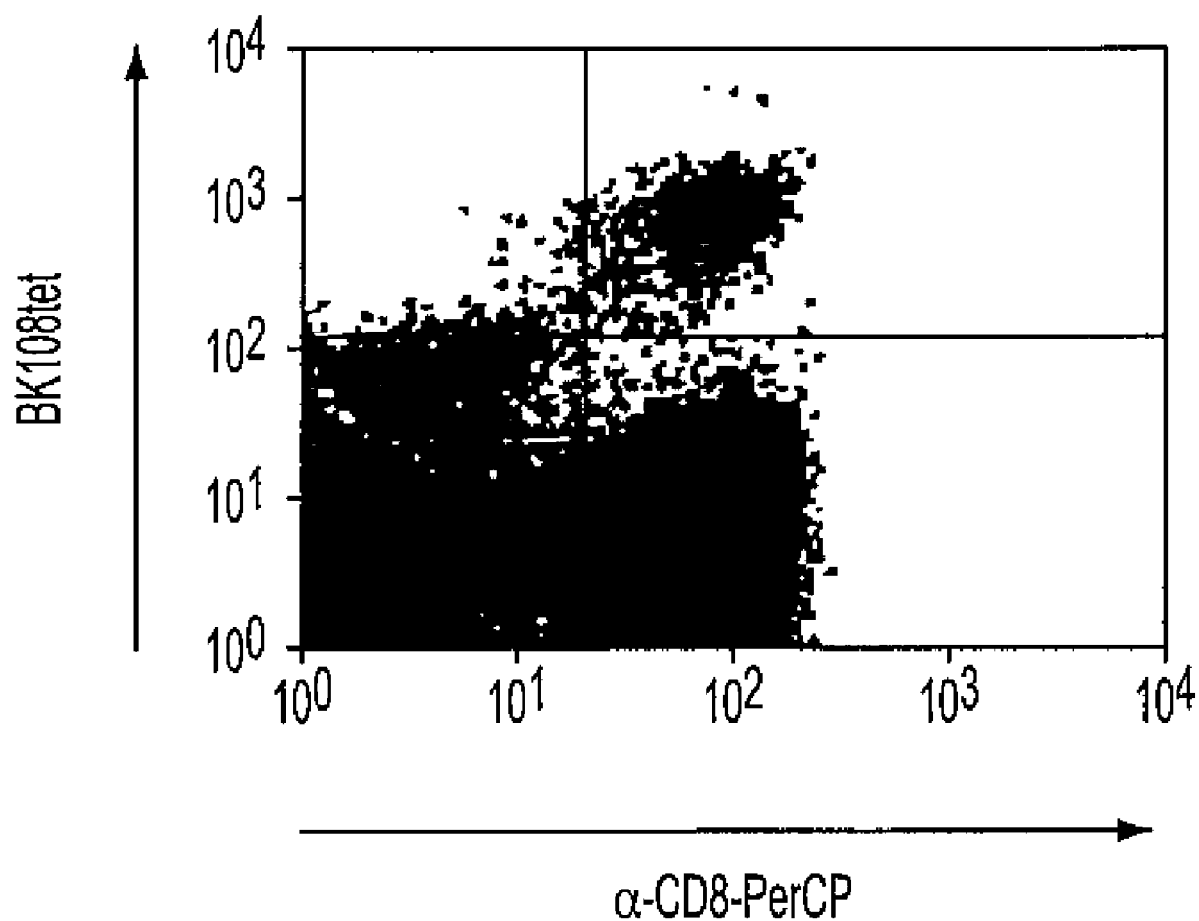
Figure 11A:
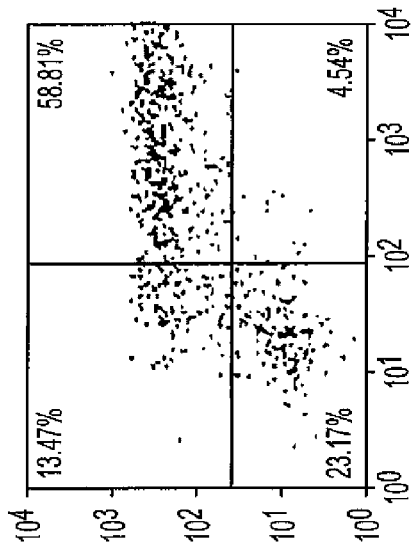
Figure 11B:
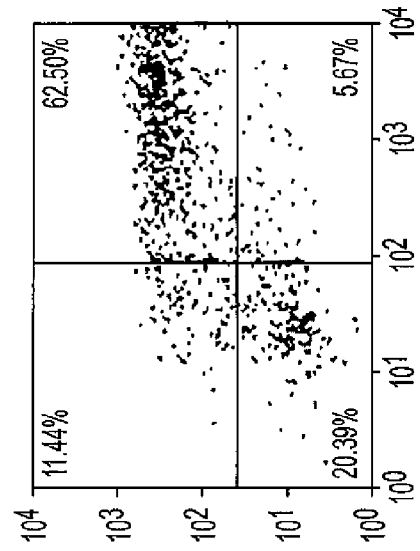
Figure 11C:
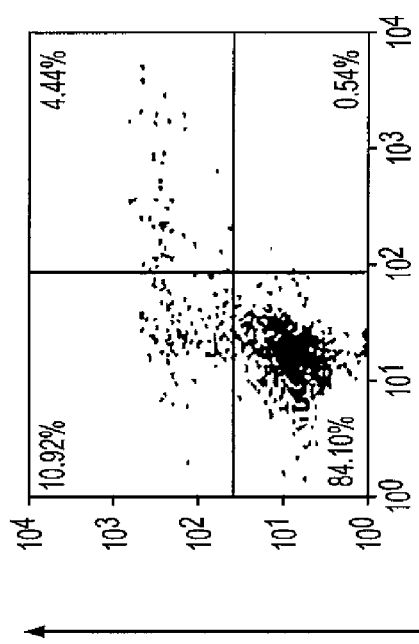
Figure 11D:
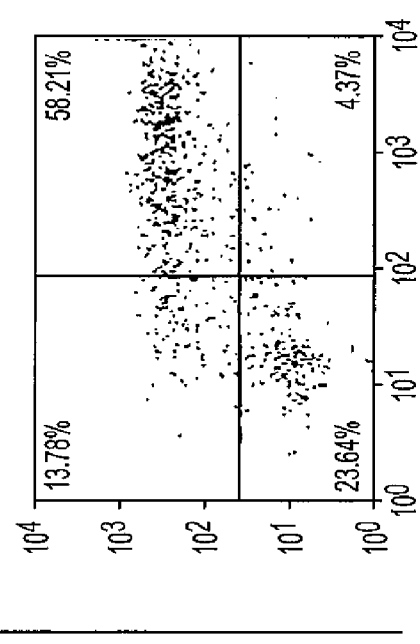

For flow analysis, a primary gate was set on lymphocytes by forward versus side scatter and in the case of the four CD107 versus IFN-γ plots, a primary gate was set on tetramer reagent-positive cells. Results of a representative assay are shown in FIGS. 10 and 11 (PBMC from normal donor #07 that had been stimulated for 2 weeks in culture with BK108 peptide in the presence of 30 U/mL rIL2). FIG. 10 is a BK108tet-APC versus CD8 plot; FIG. 11 is a quartet of cD107 versus IFN-γ plots (11A: no peptide; 11B: BK108; 11C: JC100; 11D: both BK108 and JC100). Similar results also were obtained in a repeated assay with PBMC from normal donor #04. The values in the plot quadrants indicate cell numbers as a percentage of CD8-positive/BK108 tetramer reagent-positive lymphocytes.

Stimulation in culture with either BK108 or JC100 induced IFN-γ secretion and degranulation by 58%-59% of the BK108 tetramer reagent-binding CD8$^+$ T-cells. There was a noticeable background (approximately 11%) of tetramer-reagent-binding cells with non-specific degranulation and a smaller proportion of cells (approximately 4.5%) that displayed both degranulation and IFN-γ production. This background may have been due to the stimulation of the cells under study since this background level generally is not seen with unstimulated PBMC.

Stimulation with a combination of the two peptides only slightly increased the proportion of cells that degranulated and produced IFN-γ, indicating a high degree of overlap between the cells responding to the BK108 peptide and those responding to the JC100 peptide. This indicates that the majority of the CD8$^+$ T cells bound by the BK108 tetramer reagent are functional CTL that recognize both the JCV and BKV homologs of this antigenic epitope with comparable efficiency.

Example 6

Antigenic Specificity of CD8$^+$ T-Cells

To definitively confirm that individual CD8$^+$ T cells expanded from human PBMC populations in response to stimulation with BK108 cross-recognize the JC100 epitope, the cells were co-stained with a JC100 peptide HLA-A2 tetramer reagent labeled with phycoerythrin (JC100tet-PE) and BK108tet-APC and subjected to flow cytometry. This assay distinguished among cells binding either or both of the two tetramer reagents.

Figure 12A:
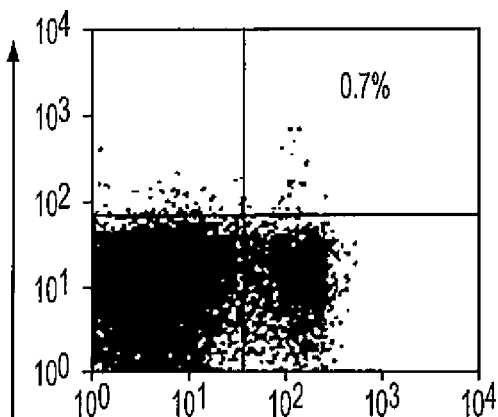
FIG. 12 shows fluorescence-activated cell sorting results for PBMC and peptide-stimulated cell cultures from a kidney transplant recipient. The cells were labeled with either BK108tet-APC (12A, 12B and 12C) or JC100tet-PE (12D, 12E and 12F) and anti-CD8 FITC.
Figure 12D:
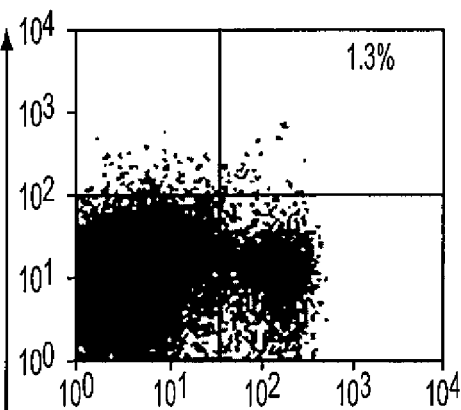

Aliquots of PBMC from kidney transplant patient KTx#02 were stimulated in culture with BK108 or with JC100 for two weeks in the presence of IL-2 to expand cells specific for those antigens. Following the expansion, the cultured cells were labeled with BK108tet-APC, JC100tet-PE or both. For purposes of comparison, unstimulated PBMC from this subject also were labeled in the same manner. The results are presented in FIGS. 12 and 13. FIGS. 12A, 12D and 13A present data from analyses performed on unstimulated, uncultured cryopreserved PBMC from kidney transplant patient Ktx#02.

Figure 12B:
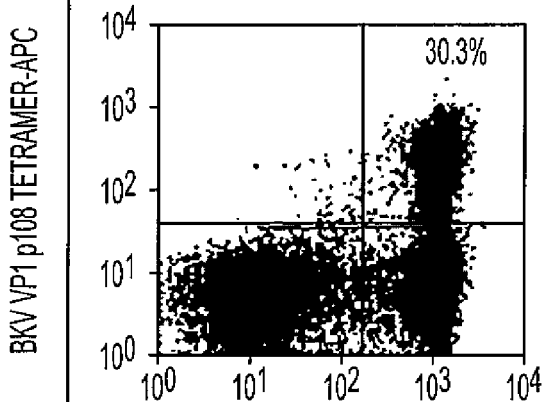
Figure 12E:
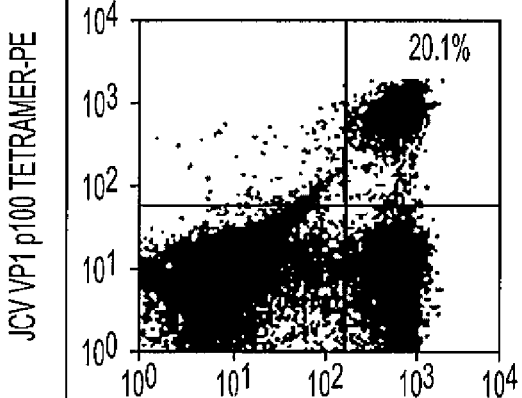
Figure 12C:
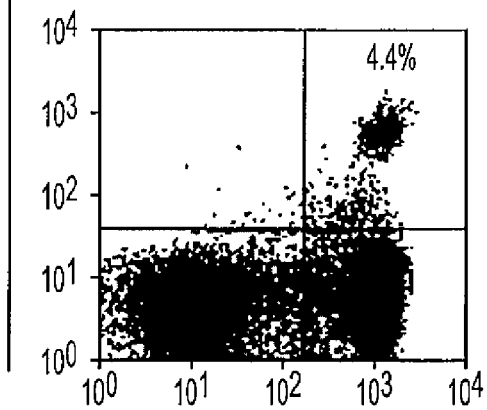
Figure 12F:
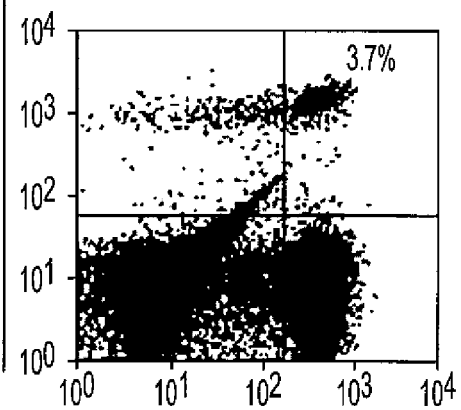

FIGS. 12B, 12E and 13B present data from analyses of an aliquot of the same PBMC, but which have been stimulated in culture with BK108 peptide in the presence of rIL2. FIGS. 12C, 12F and 13C represent analyses on an aliquot of these PBMC stimulated in culture with JC100 peptide in the presence of rIL2. The cells were labeled with BK108tet-APC (FIGS. 12A, 12B and 12C), JC100tet-PE (FIGS. 12D, 12E and 12F) or both (FIGS. 13A, 13B and 13C). The values shown in the plot quadrants indicate tetramer-binding cell numbers as percentages of CD8$^+$ lymphocytes. The majority of labeled cells in the two in vitro-stimulated cultures bound both the JCV and the BKV tetramer reagents. In the absence of in vitro stimulation, labeled cells were very infrequent and difficult to distinguish from background, however staining with both labeled tetramer reagents was able to resolve these cells. The frequency of double-labeled cells in the unstimulated PBMC population was approximately 0.6% of CD8$^+$ lymphocytes in this sample. The double tetramer-positive population within the unstimulated PBMC is circled for emphasis (FIG. 13A).

In vitro stimulation using BK108 (FIGS. 12D, 12E and 12F) expanded a sizeable population of cells that bound tetramer reagent (30.3% binding the BKV tetramer reagent and 20.1% binding the JVC tetramer reagent). The majority (84%) of the cells bound both the BKV and JVC tetramer reagents (see FIG. 13B). Stimulation with JC100 expanded a smaller population of tetramer reagent binding cells (4.4% binding the BKV tetramer reagent and 3.7% binding the JVC tetramer reagent; see FIGS. 12C and 12F). This difference in expansion efficiency could reflect a higher affinity of the CTL precursors within the PBMC for the BKV sequence.

A somewhat smaller majority (63%) of tetramer reagent binding cells bound both tetramer reagents (FIG. 13C). This difference could reflect JCV peptide-stimulated expansion of a population of cells that bind the JCV tetramer reagent but not the BKV tetramer reagent. Therefore, the effect of varying the relative amounts of the two tetramer reagents used to label these samples was tested using competitive titration. Increasing the amount of JC100 tetramer reagent while keeping the amount of corresponding BKV reagent constant did not alter the proportion of the CD8$^+$ cells binding either or both tetramer reagent. Thus, the high degree of cross-reactivity between the BKV and JCV variants of this cellular epitope was confirmed.

Example 7

In Vivo Processing of VP1 Generates the BK44 Peptide Epitope

JC36 (SITEVECFL; SEQ ID NO:6), which differs at the C terminal position from the corresponding BKV VP1 sequence, BK44 (AITEVECFL; SEQ ID NO:5), has been described as a functional HLA-A*02-restricted cellular epitope in humans. See Du Pasquier et al., *J. Virol.* 77:11918-11926, 2003; Du Pasquier et al., *J. Virol.* 78:10206-10210, 2004; Koralnik et al., *J. Immunol.* 168:499-504, 2002.

A well-known transgenic mouse model was used to test whether the BK44 peptide was generated by in vivo cellular processing of BKV VP1 and displayed on the surface of antigen-presenting cells. Transgenic HHD-II mice (4 per group) were immunized intraperitoneally with $3 \times 10^7$ plaque forming units of rMVA-BKV VP1. Two weeks after immunization, the mice were sacrificed, spleens harvested, and the splenocytes co-cultivated with syngeneic irradiated BK44 peptide-pulsed naïve mouse splenocytes. After one week of in vitro stimulation, the cultured cells were tested for specific cytotoxicity versus A2-Jurkat cells (pulsed with BK44 or JC36 peptide) and in ICC assays for IFN-γ production on peptide stimulation. Results show that the transgenic murine CTL elicited by immunization with the BKV epitope peptide recognized both the BKV and JCV homologs, with comparable affinity. See FIGS. 14-18.

FIG. 14 shows killing by BK44-immune splenocytes of targets presenting BK44 (diamonds), JC36 (squares) or control HIV peptide (triangles). FIG. 15 provides results from intracellular cytokine assays performed on the same cells. Stimulation with BK44 peptide induced the secretion of IFN-γ by CD8$^+$ cells. Thus, protective immune responses against the BK44 peptide epitope can protect against JCV by cross-recognition of the JC36 epitope. In addition, this peptide should protect against SV40, which has a previously identified epitope, SV44 (SFTEVECFL; SEQ ID NO:7), because this sequence differs by only one amino acid from the JCV sequence and two amino acids from the BKV sequence (see Table I).

FIGS. 16 and 17 show representative data from analyses of an aliquot of PBMC from a normal donor (Subject 4) which have been stimulated in culture with BK44 peptide in the presence of rIL2. The cells were labeled with BK44tet-APC (FIG. 16A), JC36tet-PE (FIG. 16B) or both (FIG. 17). When obtaining the data shown in FIG. 17, the flow cytometer was gated on CD8$^+$ lymphocytes. The majority of labeled cells in the in vitro-stimulated cultures bound both the JVC and the BKV tetramer reagents, as shown by all the tetramer reagent-positive cells in the plot of FIG. 17 being in the upper right quadrant.

FIG. 18 summarizes the data from analyses of the type illustrated in FIGS. 16 and 17 on PBMC from 8 healthy normal HLA-A*02 donors. Subjects 3, 4 and 7 harbored populations of CTL that could be expanded on stimulation with the BK44 peptide and that were labeled with both the BK44tet-APC and JC36tet-PE tetramer reagents. In addition, subjects 5 and 6 may have had weaker responses to these epitopes. The data indicate that CTL responses to the BK44 and/or JC36 epitopes are frequent in healthy adults expressing the HLA-A*02 allele.

Example 8

Vaccination Against Polyomavirus

A therapeutically active (immune system modifying) antigenic peptide BK108 (SEQ ID NO:1), BK107 (SEQ ID NO:2) or BK44 (SEQ ID NO:5), according to the present invention, is administered to an immunosuppressed patient or other person in need of polyomavirus immunity modification, either polyomavirus-seropositive or polyomavirus-seronegative. The patient can be, for example, a kidney transplant recipient patient or donor, or other solid organ or stem cell transplant recipient or donor, or an AIDS or cancer patient. The administration is given in single or multiple doses separated by a given number of days or weeks.

The therapeutically active antigenic peptides can be formulated according to any known manner which is judged to be advantageous for the particular individual by a person of skill. For example, each or both of the peptides may be administered (1) as a vaccine peptide, lipidated or unlipidated, optionally in combination with a helper peptide and/or an adjuvant), (2) as a DNA or other nucleic acid (or a vector containing such a nucleic acid) that expresses the peptide, optionally including an adjuvant, either separate or fused to the nucleic acid, (3) in the form of antigen presenting cells that present the peptide on their surface, for example T cells or dendritic cells, or (4) in the form of artificial antigen presenting cells such as described in Oelke et al., *Nat. Med.* 9:619-625, 2003, the disclosures of which are hereby incorporated by reference.

For peptide formulations, the patient preferably is administered about 0.5-20 mg naked peptide, subcutaneously or intranasally in a suitable carrier. Preferably, the formulation also contains a CpG DNA adjuvant and a T helper peptide, and may also contain other ingredients, for example diluents, preservatives, buffers, anesthetics, fragrances and the like. For viral vaccines, the patient preferably is administered 106-109 infectious units of an MVA viral recombinant that contains and expresses DNA that encodes the peptide or a fusion of the peptide and a T helper peptide, under the control of a suitable promoter. Alternatively, the patient is injected intramuscularly with about 0.1-5 mg endotoxin-free DNA diluted in sterile saline or any other suitable pharmaceutical carrier, according to known methods. For cellular vaccine compositions, T cells transfected in vitro with the DNA-based vaccine discussed above are administered intravenously.

Example 9

Immune Responses to BK108, JC108, BK44 and JC36 in Normal Donors Expressing HLA-A2

The prevalence of immune responses to the BK108, JC100, BK44 and JC36 epitopes was evaluated in a panel of 30 healthy immunocompetent volunteers expressing HLA-A2 using the methodologies described in Example 6 (expansion of PBMC by stimulation with peptide followed by tetramer labeling and flow analysis). Results are presented in FIGS. 19-22 and Table IV, below. The volunteers were randomly selected without prior knowledge of their polyomavirus serostatus. Not all combinations of peptide in vitro stimulation and tetramer reagent labeling were performed on samples from all 30 donors and double tetramer labeling was not performed on samples that were negative with the single tetramers. FIG. 19 shows staining results from flow cytometry using BK108 tetramer reagent. FIG. 20 shows the same data using JC100 tetramer reagent. FIGS. 21 and 22 provide data from double-staining cytometry with both BK108 and JC100 tetramer reagent after in vitro stimulation with BK108 or peptide, respectively.

Table IV

Polyomavirus Immune Response Survey.

| Donor | HLA A1 | HLA A2 | HLA B1 | HLA B2 | CMV | IVS with BKVp108 | | | IVS with JVCp100 | | | IVS with BKVp44 | | |
|---|---|---|---|---|---|---|---|---|---|---|---|---|---|---|
| | | | | | | % tet BKVp108 | % tetJCV p100 | BOTH | % tet BKVp108 | % tetJCV p100 | BOTH | % tet BVKp44 | % tet JCVp36 | BOTH |
| ND #01 | 201 | 2403 | 801 | 1517 | POS | 0.3 | N/A | N/A | N/A | N/A | N/A | 1.89 | 1.72 | 1.79 |
| ND #02 | 201 | | 3501 | 4402 | POS | 0.15 | N/A | N/A | N/A | N/A | N/A | N/A | N/A | N/A |
| ND #03 | 2 | 24 | 21 | 3502 | POS | 0.26 | N/A | N/A | N/A | N/A | N/A | 0 | 0.01 | 0.02 |
| ND #04 | 201 | 2601 | 801 | 3801 | NEG | 2.54 | N/A | N/A | N/A | N/A | N/A | N/A | N/A | N/A |
| ND #05 | 202 | 6801 | 702 | 4002 | POS | 0.04 | N/A | N/A | N/A | N/A | N/A | N/A | N/A | N/A |
| ND #06 | 201 | | 4402 | 5701 | POS | 0.25 | N/A | N/A | N/A | N/A | N/A | N/A | N/A | N/A |
| ND #07 | 201 | 101 | 801 | 1401 | NEG | 3.49 | N/A | N/A | N/A | N/A | N/A | N/A | N/A | N/A |
| ND #08 | 201 | 3201 | 1302 | 5101 | POS | 0.09 | N/A | N/A | N/A | N/A | N/A | 6.2 | 6.6 | 5.7 |
| ND #09 | 205 | 6601 | 1801 | 5001 | POS | 0.09 | N/A | N/A | N/A | N/A | N/A | 0 | 0 | 0 |
| ND #10 | 201 | 301 | 702 | 4901 | NEG | 0.08 | N/A | N/A | N/A | N/A | N/A | 0.33 | 0.7 | 0.17 |
| ND #11 | 208 | 2901 | 4403 | 4901 | POS | 0.06 | 0.02 | N/A | 0.04 | 0.02 | 0 | 0 | 0 | 0 |
| ND #12 | 202 | 2501 | 1302 | 1501 | POS | 0.04 | 0.01 | N/A | 0.05 | 0 | 0 | 0 | 0.08 | 0 |
| ND #13 | 201 | 2601 | 4006 | OS | POS | 0 | 0.06 | N/A | 0 | 0 | 0 | 0.13 | 0.04 | 0 |
| ND #14 | 2 | 3 | 18 | 35 | POS | 0.07 | 0 | 0.02 | 0.16 | 0.28 | 0 | 14.7 | 15 | 13.2 |
| ND #15 | 205 | 301 | 702 | 3001 | POS | 0.12 | 0 | 0 | 0.06 | 0 | 0 | 0 | 0 | 0 |
| ND #16 | 201 | 2501 | 3503 | 4001 | NEG | 0.06 | 0.03 | N/A | 0 | 0 | 0 | N/A | N/A | N/A |
| ND #17 | 202 | 3101 | 1801 | 4402 | POS | 0.1 | 0 | N/A | 0.48 | 0.59 | 0.26 | 3.14 | 3.07 | 2.63 |
| ND #18 | 2 | 3 | 44 | 62 | POS | 0 | 0 | N/A | 0 | 0 | N/A | 3.78 | 3.65 | 3.38 |
| ND #19 | 2 | | 44 | 61 | POS | 0 | 0 | N/A | 0 | 0 | N/A | N/A | N/A | N/A |
| ND #20 | 2 | 23 | 7 | 62 | POS | 0 | 0 | N/A | 0 | 0 | N/A | N/A | N/A | N/A |
| ND #21 | 202/201 | 1101 | 702 | 1501 | POS | 0 | 0 | N/A | 4.59 | 3.5 | 5.17 | N/A | N/A | N/A |
| ND #22 | 2 | 32 | 14 | 62 | POS | 0.06 | 0 | N/A | 0 | 0 | N/A | N/A | N/A | N/A |
| ND #23 | 2 | 68 | 51 | 62 | POS | 0 | 0 | N/A | 0 | 0.09 | N/A | 0.1 | 0.1 | 0.1 |
| ND #24 | 201 | 205 | 3001 | 5703 | POS | 0.04 | 0.04 | N/A | 0.04 | 0 | N/A | 0.07 | 0.07 | 0 |
| ND #25 | 201 | 2402 | 3501 | 4001 | POS | 0.06 | 0.06 | N/A | 0 | 0 | N/A | N/A | N/A | N/A |
| ND #26 | 201 | 301 | 702 | 3501 | POS | 0 | 0.04 | N/A | 0.13 | 1.36 | 0.04 | N/A | N/A | N/A |
| ND #27 | 201 | 2402 | 1501 | 2705 | POS | 0.67 | 0.46 | 0.3 | 5.1 | 5.1 | 4.3 | 6.7 | 6.2 | 6.1 |
| ND #28 | 201 | | 702 | 4001 | NEG | 0.04 | 0 | N/A | 0.03 | 0 | N/A | 0.01 | 0 | 0 |
| ND #29 | 2 | | 51 | 55 | POS | 0 | 0.06 | N/A | 0 | 0.08 | N/A | 0.63 | 0.05 | 0 |
| ND #30 | 1 | 2 | 8 | 44 | POS | 0.09 | 0.1 | N/A | 0.8 | 1.05 | 0.9 | N/A | N/A | N/A |

N/A indicates data not available;
OS indicates off study.

With the BK108 tetramer reagent, 4 of 30 and 5 of 20 individuals were positive for staining after in vitro stimulation with BK108 and JC100 peptide, respectively. For JC100 tetramer reagent, 2 of 20 and 6 of 20 individuals were positive. Both the BK44 and JC36 tetramer reagents positively stained cells from 8 of 17 individuals tested after in vitro stimulation with BK44 peptide. Therefore, for this incomplete data set, 70.6% (12/17) individuals had mounted a response to either BK44/JC36 or BK108/JC100 epitopes. Subjects responding to both these epitopes formed 17.6% (3/17) of the group.

Since the in vitro stimulation experiments with JC36 were not done, the frequency of subjects with responses to either BK44/JC36 or BK108/JC100 epitopes and the frequency of subjects with response to BK44/JC36 and to BK108/JC100 epitopes likely is higher than these data alone show. This panel of 30 individuals was assembled with no information as to their BKV or JCV seropositivity, therefore it is clear that a very high proportion of healthy HLA-A2 individuals have immune responses to at least one form of these two human polyomavirus epitopes.

The invention claimed is:

1. A polyomavirus diagnostic reagent which comprises a peptide, wherein said peptide is selected from the group consisting of LLMWEAVTV (SEQ ID NO:1); NLLMWEAVTV (SEQ ID NO:2) and AITEVECFL (SEQ ID NO:5).

2. The polyomavirus diagnostic reagent of claim 1, wherein said peptide is LLMWEAVTV (SEQ ID NO:1).

3. The polyomavirus diagnostic reagent of claim 1, wherein said peptide is NLLMWEAVTV (SEQ ID NO:2).

4. The polyomavirus diagnostic reagent of claim 1, wherein said peptide is AITEVECFL (SEQ ID NO:5).

5. The polyomavirus diagnostic reagent of claim 1, wherein said polyomavirus is BK virus.

6. The polyomavirus diagnostic reagent of claim 1, wherein said polyomavirus is JC virus.

7. The polyomavirus diagnostic reagent of claim 1, wherein said polyomavirus is SV40.

8. The polyomavirus diagnostic reagent of claim 1, which is a tetramer reagent.

9. The polyomavirus diagnostic reagent of claim 1 which is a multimer reagent.

10. The polyomavirus diagnostic reagent of claim 1 which is an MHC-I-immunoglobulin dimer reagent.

* * * * *

UNITED STATES PATENT AND TRADEMARK OFFICE
CERTIFICATE OF CORRECTION

PATENT NO. : 7,662,912 B2  Page 1 of 1
APPLICATION NO. : 12/273808
DATED : February 16, 2010
INVENTOR(S) : Lacey It is certified that error appears in the above-identified patent and that said Letters Patent is hereby corrected as shown below:

| Column | Line | Correction |
|---|---|---|
| 11 | 8 | Change "HHDII" to --HHD-II-- |
| 15 | 32 | Change "tetramer-re-" to --tetramer re- -- |
| 18 | 16 | delete ")" after "adjuvant" |
| 18 | 32-33 | Change "106-109" to --$10^6$-$10^9$-- |
| 18 | 45 | Change "JC108" to --JC100-- |
| 18 | 67 | insert --JC100-- between "or" and "peptide" |
| 19 | 40 | Change "($^{12}/_{17}$)" to --(12/17)-- |
| 19 | 43 | Change "($^{3}/_{17}$)" to --(3/17)-- |

Signed and Sealed this

Eighteenth Day of May, 2010

David J. Kappos
*Director of the United States Patent and Trademark Office*